US011292973B2

(12) United States Patent
Sundararaman et al.

(10) Patent No.: US 11,292,973 B2
(45) Date of Patent: Apr. 5, 2022

(54) PROCESS AND SYSTEM FOR UPGRADING A HYDROCARBON FEED

(71) Applicant: ExxonMobil Chemical Patents Inc., Baytown, TX (US)

(72) Inventors: Ramanathan Sundararaman, Pearland, TX (US); James R. Lattner, La Porte, TX (US); Michael W. Weber, Houston, TX (US); David T. Ferrughelli, Easton, PA (US); Saurabh S. Maduskar, Houston, TX (US); Federico Barrai, Houston, TX (US); Jeevan S. Abichandani, Houston, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 17/031,296

(22) Filed: Sep. 24, 2020

(65) Prior Publication Data

US 2021/0130711 A1    May 6, 2021

Related U.S. Application Data

(60) Provisional application No. 62/929,535, filed on Nov. 1, 2019.

(51) Int. Cl.
*C10G 69/06* (2006.01)
*C07C 4/04* (2006.01)
(Continued)

(52) U.S. Cl.
CPC ............ *C10G 69/06* (2013.01); *B01J 19/245* (2013.01); *C07C 4/04* (2013.01); *C07C 4/06* (2013.01);
(Continued)

(58) Field of Classification Search
None
See application file for complete search history.

(56) References Cited

U.S. PATENT DOCUMENTS 7,972,498 B2    7/2011  Buchanan et al.
2011/0180456 A1  7/2011  Davis et al.
(Continued)

FOREIGN PATENT DOCUMENTS

WO    2012/099671    7/2012

*Primary Examiner* — Tam M Nguyen

(57) ABSTRACT

Processes and systems for upgrading a hydrocarbon feed. The process can include feeding a hydrocarbon feed, catalyst particles, and molecular hydrogen ($H_2$) into a separation zone. The hydrocarbon feed and $H_2$ can be contacted in the presence of the catalyst particles under hydrotreating conditions in the separation zone that can include contacting under a total pressure of less than 3,500 kilopascals-gauge. The $H_2$ can be fed into the separation zone at a rate of no greater than 270 cubic meters of $H_2$ per cubic meter of the hydrocarbon feed, where the volume of $H_2$ and hydrocarbon feed are based on a temperature of 25 C and a pressure of 101 kilopascals-absolute. A vapor phase hydrocarbon stream and a liquid phase hydrocarbon stream can be obtained from the separation zone. At least a portion of the vapor phase hydrocarbon stream can be fed into a pyrolysis reaction zone to produce a pyrolysis effluent.

24 Claims, 2 Drawing Sheets

(51) Int. Cl.
*C07C 4/06* (2006.01)
*B01J 19/24* (2006.01)

(52) U.S. Cl.
CPC ............... *B01J 2219/0004* (2013.01); *C10G 2300/1003* (2013.01); *C10G 2300/107* (2013.01); *C10G 2300/1077* (2013.01); *C10G 2300/202* (2013.01); *C10G 2300/301* (2013.01); *C10G 2300/4006* (2013.01); *C10G 2300/4012* (2013.01); *C10G 2400/20* (2013.01)

(56) References Cited

U.S. PATENT DOCUMENTS

| | | | |
|---|---|---|---|
| 2013/0289144 A1* | 10/2013 | Steyn | C10G 2/332 518/712 |
| 2014/0054198 A1* | 2/2014 | Podrebarac | C10G 65/00 208/57 |
| 2019/0040329 A1* | 2/2019 | Moore | C10G 69/04 |
| 2019/0330544 A1* | 10/2019 | Dubreuil | B01J 37/18 |
| 2021/0154653 A1* | 5/2021 | Boualleg | B01J 23/892 |
| 2021/0154654 A1* | 5/2021 | Boualleg | B01J 6/001 |
| 2021/0331145 A1* | 10/2021 | Dubreuil | B01J 37/084 |

* cited by examiner

PROCESS AND SYSTEM FOR UPGRADING A HYDROCARBON FEED

CROSS-REFERENCE TO RELATED APPLICATIONS

This application claims the benefit of and priority to U.S. Provisional Application Ser. No. 62/929,535, filed Nov. 1, 2019, the content of which is herein incorporated by reference.

FIELD

This disclosure relates to processes and systems for upgrading a hydrocarbon feed. In particular, this disclosure relates to processes and systems for converting a hydrocarbon feed by pyrolysis to produce various products, e.g., olefins and fuel oil products.

BACKGROUND

Steam cracking, also referred to as pyrolysis, has long been used to crack various hydrocarbon feeds into olefins, preferably light olefins such as ethylene, propylene, and butenes. Conventional steam cracking utilizes a pyrolysis reactor ("steam cracker") that has two main sections: a convection section and a radiant section. The hydrocarbon feed typically enters the convection section of the furnace as a liquid (except for light feedstocks that typically enter as a vapor) where the feedstock is typically heated and vaporized by indirect heat exchange with a hot flue gas from the radiant section and by direct contact with steam. The vaporized feedstock and steam mixture is fed into the radiant section where the cracking takes place. The resulting pyrolysis effluent, including olefins, leaves the pyrolysis reactor for further downstream processing, including quenching.

Conventional pyrolysis reactors do not have the flexibility to process residues, crudes, or many residues, crude gas oils, or naphthas that are contaminated with non-volatile components. Non-volatile components, if present in the feed, typically cause fouling within the radiant section of the pyrolysis reactor. An external vaporization drum or flash drum has been implemented to separate vaporized hydrocarbons from liquid hydrocarbons to address the fouling problems in the pyrolysis reactor. The vaporized hydrocarbons are then cracked in the pyrolysis reactor and the liquid hydrocarbons that include nonvolatile components are removed and used as fuel. The liquid hydrocarbons, however, still contain a substantial quantity of hydrocarbons which, if converted into higher-value lighter hydrocarbons such as olefins via cracking, would bring substantial additional value to the crude oil feed. Thus, for decades the petrochemical industry has been trying to take advantage of relatively low-cost heavy crude oil to make substantial quantities of valuable chemicals such as olefins. The large amount of non-volatiles in the low-cost heavy crude oil, however, requires extensive and expensive processing.

There is a need, therefore, for improved processes and systems for upgrading hydrocarbon feeds to produce valuable chemical products such as olefins. This disclosure satisfies this and other needs.

SUMMARY

The present inventors have devised processes and systems for converting a hydrocarbon feed by pyrolysis. In certain embodiments, the process can include feeding a hydrocarbon feed, a plurality of catalyst particles, and molecular hydrogen into a separation zone. The catalyst particles can include a transition metal element. At least a portion of the hydrocarbon feed and at least a portion of the molecular hydrogen can be contacted in the presence of the catalyst particles under hydrotreating conditions in the separation zone. The hydrocarbon feed and the molecular hydrogen can be contacted under a total pressure of less than 3,500 kilopascals-gauge. The molecular hydrogen can be fed into the separation zone at a rate of no greater than 270 cubic meters of molecular hydrogen per cubic meter of the hydrocarbon feed, where the volume of molecular hydrogen and hydrocarbon feed are based on a temperature of 25° C. and a pressure of 101 kilopascals-absolute. A vapor phase hydrocarbon stream and a liquid phase hydrocarbon stream can be obtained from the separation zone. At least a portion of the vapor phase hydrocarbon stream can be fed into a pyrolysis reaction zone to produce a pyrolysis effluent that can include olefins and molecular hydrogen.

In certain other embodiments, the process for converting a hydrocarbon feed by pyrolysis can include heating a hydrocarbon feed to produce a heated hydrocarbon feed that can include a vapor phase and a liquid phase. The heated hydrocarbon feed can be fed into a first separation zone. A first vapor phase hydrocarbon stream and a first liquid phase hydrocarbon stream can be obtained from the first separation zone. The first liquid phase hydrocarbon stream, a plurality of catalyst particles, and molecular hydrogen can be fed into a second separation zone, wherein the catalyst particles that can include a transition metal element. At least a portion of the first liquid phase hydrocarbon stream and at least a portion of the molecular hydrogen can be contacted in the presence of the catalyst particles under hydrotreating conditions in the second separation zone. The first liquid phase hydrocarbon and the molecular hydrogen can be contacted under a total pressure of less than 3,500 kilopascals-gauge. The molecular hydrogen can be fed into the second separation zone at a rate of no greater than 270 cubic meters of molecular hydrogen per cubic meter of the hydrocarbon feed, where the volume of molecular hydrogen and hydrocarbon feed are based on a temperature of 25° C. and a pressure of 101 kilopascals-absolute. A second vapor phase hydrocarbon stream and a second liquid phase hydrocarbon stream can be obtained from the second separation zone. At least a portion of the first vapor phase hydrocarbon stream and at least a portion of the second vapor phase hydrocarbon stream can be fed into a pyrolysis reaction zone to produce a pyrolysis effluent that can include olefins and molecular hydrogen.

In certain embodiments, the system for converting a hydrocarbon feed by pyrolysis can include a first vapor-liquid separator adapted for receiving a hydrocarbon feed, a plurality of catalyst particles, and molecular hydrogen, allowing at least a portion of the hydrocarbon feed to contact at least a portion of the molecular hydrogen in the presence of the catalyst particles under hydrotreating conditions, discharging a first vapor phase hydrocarbon stream, and discharging a first liquid phase hydrocarbon stream. The catalyst particles can include a transition metal element. The hydrocarbon feed and the molecular hydrogen can be contacted under a total pressure of less than 3,500 kilopascals-gauge. The molecular hydrogen can be fed into the first vapor-liquid separator at a rate of no greater than 270 cubic meters of molecular hydrogen per cubic meter of the hydrocarbon feed, where the volume of molecular hydrogen and hydrocarbon feed are based on a temperature of 25° C. and a pressure of 101 kilopascals-absolute. The system can also include a pyrolysis reactor adapted for receiving the first vapor phase hydrocarbon stream, heating the first vapor phase hydrocarbon stream to effect pyrolysis of at least a portion of the first vapor phase hydrocarbon stream, and discharging a pyrolysis effluent stream. The system can also include a quenching section adapted for receiving the pyrolysis effluent stream, quenching the pyrolysis effluent stream, and discharging a quenched pyrolysis effluent stream. The system can also include a second vapor-liquid separator adapted for receiving the quenched pyrolysis effluent stream, separating the quenched pyrolysis effluent stream to obtain a second vapor phase hydrocarbon stream that can include olefins and a second liquid phase hydrocarbon stream that can include pyrolysis tar, discharging the second vapor phase hydrocarbon stream, and discharging the second liquid phase hydrocarbon stream. The system can also include a hydroprocessing unit adapted for receiving the first liquid phase hydrocarbon stream and the second liquid phase hydrocarbon stream, hydroprocessing the first liquid phase hydrocarbon stream and the second liquid phase hydrocarbon stream under hydroprocessing conditions to produce a hydrocarbon fuel oil stream that can include less than 5,000 wppm of sulfur, and discharging the hydrocarbon fuel oil stream.

In certain other embodiments, the system can include a first vapor-liquid separator adapted for receiving a hydrocarbon feed, separating the hydrocarbon feed into a first vapor phase hydrocarbon stream and a first liquid phase hydrocarbon stream, discharging the first vapor phase hydrocarbon stream, and discharging the first liquid phase hydrocarbon stream. The system can also include a second vapor-liquid separator adapted for receiving the first liquid phase hydrocarbon stream, a plurality of catalyst particles, and molecular hydrogen, allowing at least a portion of the first liquid phase hydrocarbon stream to contact at least a portion of the molecular hydrogen in the presence of the catalyst particles under hydrotreating conditions, discharging a second vapor phase hydrocarbon stream, and discharging a second liquid phase hydrocarbon stream. The first liquid phase hydrocarbon stream and the molecular hydrogen can be contacted under a total pressure of less than 3,500 kilopascals-gauge. The molecular hydrogen can be fed into the second vapor-liquid separator at a rate of no greater than 270 cubic meters of molecular hydrogen per cubic meter of the hydrocarbon feed, where the volume of molecular hydrogen and hydrocarbon feed are based on a temperature of 25° C. and a pressure of 101 kilopascals-absolute. The system can also include a pyrolysis reactor adapted for receiving the first vapor phase hydrocarbon stream and the second vapor phase hydrocarbon stream, heating the first vapor phase hydrocarbon stream and the second vapor phase hydrocarbon stream to effect pyrolysis of at least a portion of the first vapor phase hydrocarbon stream and the second vapor phase hydrocarbon stream, and discharging a pyrolysis effluent stream. The system can also include a quenching section adapted for receiving the pyrolysis effluent stream, quenching the pyrolysis effluent stream, and discharging a quenched pyrolysis effluent stream. The system can also include a third vapor-liquid separator adapted for receiving the quenched pyrolysis effluent stream, separating the quenched pyrolysis effluent stream to obtain a third vapor phase hydrocarbon stream that can include olefins and a third liquid phase hydrocarbon stream that can include pyrolysis tar, discharging the third vapor phase hydrocarbon stream, and discharging the third liquid phase hydrocarbon stream. The system can also include a hydroprocessing unit adapted for receiving the second liquid phase hydrocarbon stream and the third liquid phase hydrocarbon stream, hydroprocessing the second liquid phase hydrocarbon stream and the third liquid phase hydrocarbon stream under hydroprocessing conditions to produce a hydrocarbon fuel oil stream that can include less than 5,000 wppm of sulfur, and discharging the hydrocarbon fuel oil stream.

DETAILED DESCRIPTION

Figure 1:
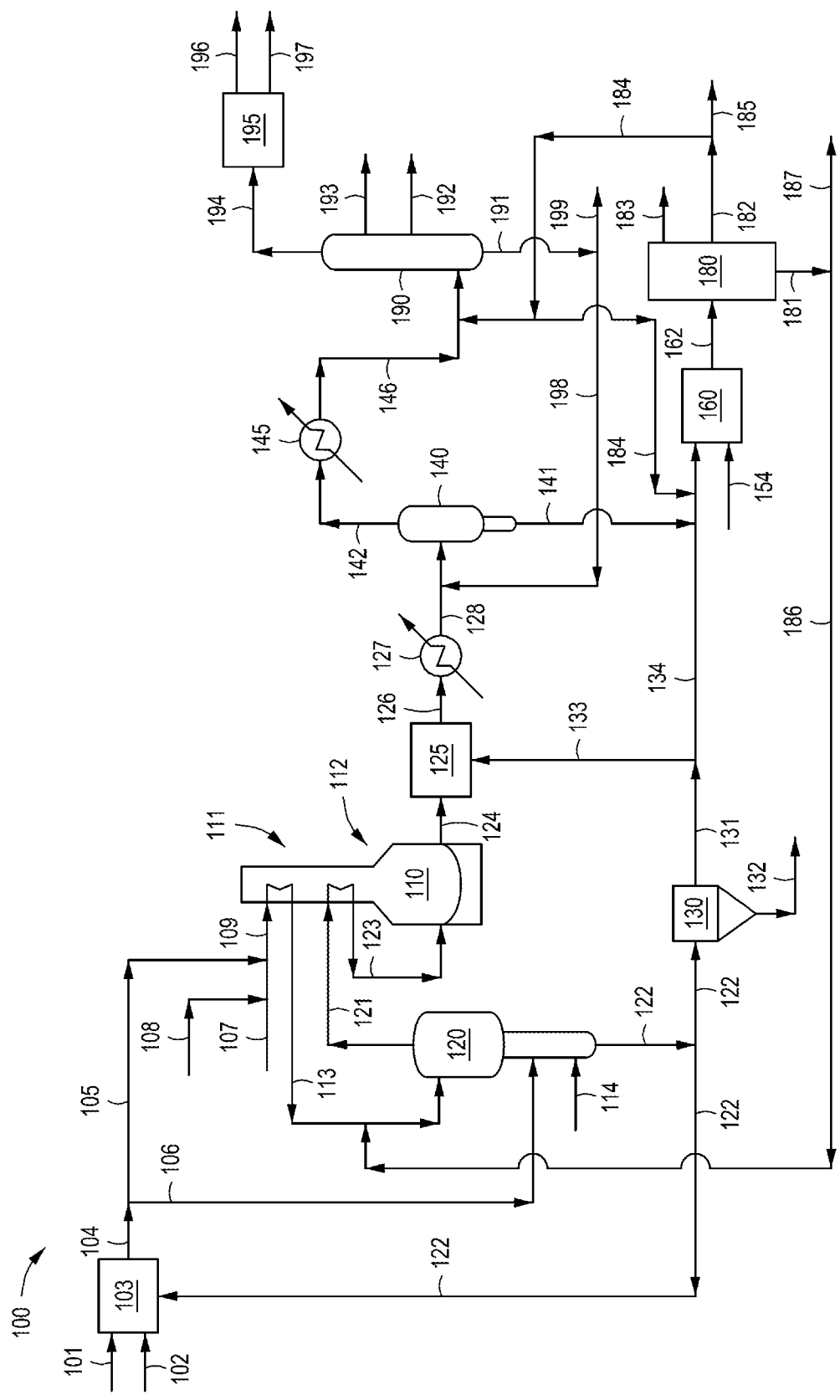
FIG. 1 depicts an illustrative system for converting a petroleum feed by pyrolysis, according to one or more embodiments described.

Various specific embodiments, versions and examples of this disclosure will now be described, including preferred embodiments and definitions that are adopted herein for purposes of understanding the claimed invention. While the following detailed description gives specific preferred embodiments, those skilled in the art will appreciate that these embodiments are exemplary only, and that this disclosure may be practiced in other ways. For purposes of determining infringement, the scope of this disclosure will refer to any one or more of the appended claims, including their equivalents, and elements or limitations that are equivalent to those that are recited. Any reference to the "invention" may refer to one or more, but not necessarily all, of this disclosure defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for making the measurement.

Certain embodiments and features are described herein using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated.

As used herein, the indefinite article "a" or "an" shall mean "at least one" unless specified to the contrary or the context clearly indicates otherwise. Thus, embodiments using "a pyrolysis reactor" include embodiments where one, two or more pyrolysis reactors are used, unless specified to the contrary or the context clearly indicates that only one pyrolysis reactor is used.

"Crude" or "crude oil" in this disclosure interchangeably means whole crude oil as it issues from a wellhead, production field facility, transportation facility, or other initial field processing facility, and/or crude that has been processed by a step of desalting, treating, and/or other steps as may be necessary to render it acceptable for conventional distillation in a refinery. Crude as used herein is presumed to contain resid.

"Crude fractions" as used herein mean hydrocarbon fractions obtainable from fractionation of a crude.

"Resid" as used herein refers to (i) the bottoms cut of a crude distillation process that contains non-volatile components, and/or (ii) a material comprising organic compounds such as hydrocarbons having boiling points in the boiling point range of a resid in category (i). Resids of category (i) are complex mixture of heavy petroleum compounds otherwise known in the art as residuum or residual. Atmospheric resid is the bottoms product produced from atmospheric distillation of a crude where a typical endpoint of the heaviest distilled product is nominally 650° F. (343° C.), and is referred to as 650° F. (343° C.) resid. The term "nominally" herein means that reasonable experts may disagree on the exact cut point for these terms, but by no more than +/−100° F. (+/−55.6° C.) preferably no more than +/−50° F. (+/−27.8° C.). Vacuum resid is the bottoms product from a distillation column operated under vacuum where the heaviest distilled product can be nominally 1050° F. (566° C.), and is referred to as 1050° F. (566° C.) resid. This 1050° F. (566° C.) portion contains high concentration of asphaltenes, which traditionally are considered to be problematic for the steam cracker, resulting in severe fouling and potentially corrosion or erosion of the apparatus. Vacuum resid can be advantageously mixed with a crude, and/or a lighter crude fraction such as an atmospheric resid to form a suitable feed supplied to the flashing drum of the process of this disclosure. Category (ii) resid in this disclosure can include, e.g., (a) natural or synthetic polymer materials, such as polyethylene, polypropylene, polystyrene, polyvinyl chloride, and the like; (b) biofuel (e.g., biodiesel) derived from biological materials (e.g., lignin, plant waste, algae waste, and food waste); (c) biological materials such as algae, corn, soy; and (d) any mixture of one or more of (a), (b), and/or (c).

The term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of them at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn- hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

The term "non-volatile components" as used herein refers to the fraction of a petroleum feed having a nominal boiling point of at least 590° C. (1,100° F.) as measured by ASTM D6352-15 or D-2887-18. Non-volatiles include coke precursors, which are large, condensable molecules that condense in the vapor and then form coke during pyrolysis of the petroleum feed.

The term "olefin product" as used herein means a product that includes an olefin, preferably a product consisting essentially of an olefin. An olefin product in the meaning of this disclosure can be, e.g., an ethylene stream, a propylene stream, a butylene stream, an ethylene/propylene mixture stream, and the like.

The term "rich" when used in phrases such as "X-rich" or "rich in X" means, with respect to an outgoing stream obtained from a device, that the stream comprises material X at a concentration higher than in the feed material fed to the same device from which the stream is derived.

The term "lean" when used in phrases such as "X-lean" or "lean in X" means, with respect to an outgoing stream obtained from a device, that the stream comprises material X at a concentration lower than in the feed material fed to the same device from which the stream is derived.

The term "consisting essentially of" as used herein means the composition, feed, or effluent comprises a given component at a concentration of at least 60 wt %, preferably at least 70 wt %, more preferably at least 80 wt %, more preferably at least 90 wt %, still more preferably at least 95 wt %, based on the total weight of the composition, feed, or effluent in question.

The terms "channel" and "line" are used interchangeably and mean any conduit configured or adapted for feeding, flowing, and/or discharging a gas, a liquid, and/or a fluidized solids feed into the conduit, through the conduit, and/or out of the conduit, respectively. For example, a composition can be fed into the conduit, flow through the conduit, and/or discharge from the conduit to move the composition from a first location to a second location. Suitable conduits can be or can include, but are not limited to, pipes, hoses, ducts, tubes, and the like.

In this disclosure, a "reactor" includes a reaction vessel in which intended chemical reactions occur to convert a feed into a product mixture, and any equipment peripheral to the reaction vessel such as feed pre-conditioning equipment (heat exchangers, compressors, purification equipment, and the like), product mixture processing equipment (heat exchangers, compressors, separation equipment including but not limited to distillation columns, and the like), recycle management equipment (heat exchangers, compressors, and the like), reboiler, condenser, catalyst regeneration equipment, pump(s), valves, meters, and the like. Thus, a reactor can be understood as a reactor unit, or a reactor sub-system.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All concentrations herein are expressed on the basis of the total amount of the composition in question. Thus, the concentrations of the various components of the "petroleum feed" are expressed based on the total weight of the petroleum feed. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

The hydrocarbon feed can be, can include, or can be derived from petroleum, plastic material, natural gas condensate, landfill gas (LFG), biogas, coal, bio-based oils, rubber, or any mixture thereof. In certain embodiments, the hydrocarbon feed can include a non-volatile component. In certain embodiments, the petroleum can be or can include any crude or any mixture thereof, any crude fraction or any mixture thereof, or any mixture of any crude with any crude fraction. A typical crude includes a mixture of hydrocarbons with varying carbon numbers and boiling points. Thus, by using conventional atmospheric distillation and vacuum distillation, one can produce a range of fuel products with varying boiling points, e.g., naphtha, gasoline, kerosene, distillate, and tar. It is highly desired, however, to convert the large hydrocarbon molecules contained in the crude into more valuable, lighter products including but not limited to ethylene, propylene, butylenes, and the like, which can be further made into more valuable products such as polyethylene, polypropylene, ethylene-propylene copolymers, butyl rubbers, and the like.

In certain embodiments, the petroleum can be or can include: crude oil, atmospheric resid, vacuum resid, steam cracked gas oil and residue, gas oil, heating oil, hydrocrackate, atmospheric pipestill bottoms, vacuum pipestill streams including bottoms, gas oil condensate, heavy non-virgin hydrocarbon stream from refineries, vacuum gas oil, heavy gas oil, naphtha contaminated with crude, heavy residue, C4's/residue admixture, naphtha/residue admixture, hydrocarbon gases/residue admixture, hydrogen/residue admixture, gas oil/residue admixture, or any mixture thereof. Non-limiting examples of crudes can be, or can include, but are not limited to, Tapis, Murban, Arab Light, Arab Medium, and/or Arab Heavy.

In certain embodiments, the plastic material can be, or can include, but is not limited to, polyethylene terephthalate (PETE or PET), polyethylene (PE), polypropylene (PP), polyvinyl chloride (PVC), polyvinylidene chloride (PVDC), polystyrene (PS), polycarbonate (PC), polylactic acid (PLA), acrylic (PMMA), acetal (polyoxymethylene, POM), acrylonitrile-butadiene-styrene (ABS), fiberglass, nylon (polyamides, PA), polyester (PES) rayon, polyoxybenzylmethylenglycolanhydride (bakelite), polyurethane (PU), polyepoxide (epoxy), or any mixture thereof. The rubber can be or can include natural rubber, synthetic rubber, or a mixture thereof. In certain embodiments, the biogas can be produced via anaerobic digestion, e.g., the biogas produced during the anaerobic digestion of sewage. In certain embodiments, the biobased oil can be or can include oils that can degrade biologically over time. In certain embodiments, the biobased oil can be degraded via processes of bacterial decomposition and/or by the enzymatic biodegradation of other living organisms such as yeast, protozoans, and/or fungi. Biobased oils can be derived from vegetable oils, e.g., rapeseed oil, castor oil, palm oil, soybean oil, sunflower oil, corn oil, hemp oil, or chemically synthesized esters.

If the hydrocarbon feed includes material that is solid at room temperature, e.g., plastic material, coal, and/or rubber, the solid material can be reduced to any desired particle size via well-known processes. For example, if the hydrocarbon-containing feed includes solid material, the solid material can be ground, crushed, pulverized, other otherwise reduced into particles that have any desired average particle size. In certain embodiments, the solid matter can be reduced to an average particle size that can be submicron or from about 1 μm, about 10 μm or about 50 μm to about 100 μm, about 150 μm, or about 200 μm. For example, the average particle size of the hydrocarbon feedstock, if solid matter, can range from about 75 μm to about 475 μm, from about 125 μm to about 425 μm, or about 175 μm to about 375 μm.

In certain embodiments, the hydrocarbon feed can include one or more crude oils or a fraction thereof and one or more plastic materials. In certain embodiments, the hydrocarbon feed can include petroleum and one or more plastic materials, the one or more plastic materials present in an amount in a range of from 1 wt %, 3 wt %, 5 wt %, 7 wt %, 10 wt %, or 15 wt % to 20 wt %, 25 wt %, 30 wt %, 35 wt %, 40 wt %, or 45 wt %, based on the total weight of the hydrocarbon feed.

The petroleum, e.g., crude oil or fraction thereof, can act as a solvent for the plastic material and cause at least a portion of the plastic material to dissolve in the crude oil or fraction thereof. In certain embodiments, at least 30 wt %, at least 40 wt %, at least 50 wt %, at least 60 wt %, at least 70 wt %, at least 80 wt %, at least 90 wt %, or even 100 wt % of the plastic material mixed with the crude oil or fraction thereof can be solubilized in the crude oil or fraction thereof. As such, in certain embodiments, when the hydrocarbon feed includes one or more plastic materials, the hydrocarbon feed can be in the form of a solution in which the plastic material is homogeneously dispersed in the crude oil or fraction thereof.

Process for Pyrolyzing the Hydrocarbon Feed

It has been surprisingly and unexpectedly discovered that contacting a hydrocarbon feed, e.g., a petroleum feed or a fraction thereof or a petroleum feed or a fraction thereof and a plastic material, with molecular hydrogen in the presence of a plurality of catalyst particles under hydrotreating conditions in a separation zone can significantly increase an amount of hydrocarbons that can be vaporized within the separation zone. The catalyst particles can include a transition metal element. In certain embodiments, the transition metal element can be a sulfide of the transition metal element. A vapor phase hydrocarbon stream and a liquid phase hydrocarbon stream can be obtained from the separation zone. At least a portion of the vapor phase hydrocarbon stream can be fed into a pyrolysis reaction zone, e.g., a radiant section of a steam cracker furnace, to produce a pyrolysis effluent that can include olefins and molecular hydrogen. By increasing the amount of the hydrocarbon feed that can be vaporized within the separation zone, a substantial increase in an amount of hydrocarbon products, e.g., olefins, recovered from the pyrolysis reaction zone can be realized. Additionally, an amount of the liquid phase hydrocarbon stream obtained from the separation zone can be decreased, which can reduce the amount of liquid phase hydrocarbon that needs to be further processed, e.g., hydroprocessed, to produce a fuel oil or other hydrocarbon product(s).

In certain embodiments, the hydrocarbon feed, e.g., a petroleum feed or a fraction thereof or a petroleum feed or a fraction thereof and a plastic material, can be introduced into a first or initial separation zone and an overhead or first vapor phase hydrocarbon stream and a bottoms or first liquid phase hydrocarbon stream can be obtained therefrom. The first liquid phase hydrocarbon stream obtained from the first separation zone, molecular hydrogen, and the catalyst particles can be introduced into a second separation zone where the first liquid phase hydrocarbon stream can be subjected to the hydrotreating conditions. A second vapor phase hydrocarbon stream and a second liquid phase hydrocarbon stream can be obtained from the second separation zone. At least a portion of the second vapor phase hydrocarbon stream can be fed into the pyrolysis reaction zone to produce the pyrolysis effluent. In certain embodiments, at least a portion of the first vapor phase hydrocarbon stream and at least a portion of the second vapor phase hydrocarbon stream can be fed into the pyrolysis reaction zone to produce the pyrolysis effluent. The separation zone can be located within one or more separation stages or a portion thereof. The first separation zone can be located within one or more first separation stages or a portion thereof and the second separation zone can located within one or more second separation stages or a portion thereof. For example, the separation zone, first separation zone, and second separation zone can be located within an internal volume or portion thereof of a vessel such as a flashing drum or vaporization drum.

In certain embodiments, contacting the hydrocarbon feed with the molecular hydrogen in the presence of the catalyst particles in the separation zone can increase the amount of the vapor phase hydrocarbon stream recovered from the separation zone in a range of from 3 wt %, 5 wt %, or 10 wt % to about 15 wt %, 20 wt %, or 25 wt %, as compared to introducing the hydrocarbon feed into the separation zone in the absence of the molecular hydrogen and in the absence of the catalyst particles. In certain other embodiments, when a first separation zone and a second separation zone are used in combination, contacting the first liquid phase hydrocarbon feed with the molecular hydrogen in the presence of the catalyst particles in the second separation zone can increase the total amount of vaporized hydrocarbons recovered from the first and second separation zones in a range of from 5 wt %, 10 wt %, 15 wt %, 20 wt %, or 25 wt % to 30 wt %, 35 wt %, 40 wt %, 45 wt %, or 50 wt %, as compared to introducing the first liquid phase hydrocarbon feed into the second separation zone in the absence of the molecular hydrogen and in the absence of the catalyst particles.

In certain embodiments, contacting the hydrocarbon feed with the molecular hydrogen in the presence of the catalyst particles in the separation zone can increase an amount of overhead vapor recovered from a primary fractionator separating a pyrolysis effluent produced by pyrolyzing the vapor phase hydrocarbon stream obtained from the separation zone in a range of from 3 wt %, 5 wt %, or 10 wt % to about 15 wt %, 20 wt %, or 25 wt %, as compared to introducing the hydrocarbon feed into the separation zone in the absence of the molecular hydrogen and in the absence of the catalyst particles. In certain other embodiments, when a first separation zone and a second separation zone are used in combination, contacting the first liquid phase hydrocarbon stream with the molecular hydrogen in the presence of the catalyst particles in the second separation zone can increase an amount of overhead vapor recovered from a primary fractionator used to separate a pyrolysis effluent produced by pyrolyzing the first and second vapor phase hydrocarbon streams obtained from the first and second separation zones in a range of from 5 wt %, 10 wt %, 15 wt %, 20 wt %, or 25 wt % to 30 wt %, 35 wt %, 40 wt %, 45 wt %, or 50 wt %, as compared to introducing the first liquid phase hydrocarbon stream into the second separation zone in the absence of the molecular hydrogen and in the absence of the catalyst particles.

The hydrocarbon feed or the first liquid phase hydrocarbon stream (when a first and second separation zone are used) can be contacted with the molecular hydrogen in the presence of the catalyst particles under a total pressure of less than 3,500 kilopascals-gauge. In certain embodiments, hydrocarbon feed or the first liquid phase hydrocarbon stream can be contacted with the molecular hydrogen in the presence of the catalyst particles under a total pressure in a range of from 100 kilopascals-gauge, 300 kilopascals-gauge, 500 kilopascals-gauge, or 650 kilopascals-gauge to 1,000 kilopascals-gauge, 1,250 kilopascals-gauge, 1,500 kilopascals-gauge, 1,750 kilopascals-gauge, 2,000 kilopascals-gauge, 2,500 kilopascals-gauge, 2,750 kilopascals-gauge, 3,000 kilopascals-gauge, or 3,300 kilopascals-gauge.

The molecular hydrogen can be fed into the separation zone or the second separation zone at a rate of no greater than 270 cubic meters of molecular hydrogen per cubic meter of the hydrocarbon feed, where the volume of molecular hydrogen and hydrocarbon feed are based on a temperature of 25° C. and a pressure of 101 kilopascals-absolute. In certain embodiments, the molecular hydrogen can be fed into the separation zone or the second separation zone at a rate in a range of from 25 cubic meters, 36 cubic meters, 50 cubic meters, 75 cubic meters, or 100 cubic meters to 150 cubic meters, 180 cubic meters, 200 cubic meters, 225 cubic meters, 250 cubic meters, or 270 cubic meters of molecular hydrogen per cubic meter of the hydrocarbon feed, where the volume of molecular hydrogen and hydrocarbon feed are based on a temperature of 25° C. and a pressure of 101 kilopascals-absolute.

The hydrocarbon feed or the first liquid phase hydrocarbon stream can be contacted with the molecular hydrogen in the presence of the catalyst particles at a temperature in the separation zone or the second separation zone in a range of from 200° C., 255° C., 300° C., 325° C., or 350° C. to 400°, 500° C., 600° C., 650° C., 700° C., or greater. In certain embodiments, the hydrocarbon feed or the first liquid phase hydrocarbon stream can be contacted with the molecular hydrogen in the presence of the catalyst particles at a temperature in the separation zone or the second separation zone in a range of from 250° C. to 500° C., 350° C. to 500° C., or 400° C. to 650° C. or greater. The liquid phase hydrocarbon stream obtained from the separation zone or the second liquid phase hydrocarbon stream obtained from the second separation zone can have a cutoff point in a range of from 500° C. to 650° C. or greater, as measured according to ASTM D1160-18.

The molecularly hydrogen and the hydrocarbon feed or the first liquid phase hydrocarbon stream can be contacted for a residence time in a range of from 20 minutes to 4 hours. In certain embodiments, the hydrocarbon feed and the molecular hydrogen can be contacted for a residence time in a range of from 20 minutes, 30 minutes, 45 minutes, or 1 hour to 1.25 hours, 1.5 hours, 1.75 hours, 2 hours, 2.25 hours, or 2.5 hours.

The transition metal element in the catalyst particles can be fed into the separation zone or the second separation zone at a feeding rate in a range of from 25 wppm to 1,000 wppm, based on the weight of the hydrocarbon feed. In certain embodiments, the transition metal element in the catalyst particles can be fed into the separation zone or the second separation zone at a feeding rate in a range of from 25 wppm, 50 wppm, 75 wppm, 100 wppm, 150 wppm, or 175 wppm to 200 wppm, 250 wppm, 300 wppm, 400 wppm, 500 wppm, 700 wppm, 850 wppm, or 1,000 wppm, based on the weight of the hydrocarbon feed.

In certain embodiments, the hydrocarbon feed or the first liquid phase hydrocarbon stream can be contacted with the molecular hydrogen in the presence of the catalyst particles under a total pressure of less than 3,500 kilopascals-gauge, at a temperature in the separation zone or the second separation zone in a range of from 200° C. to 500° C., and for a residence time in a range of from 20 minutes to 2.5 hours, the molecular hydrogen can be fed into the separation zone or the second separation zone at a rate of no greater than 270 cubic meters of molecular hydrogen per cubic meter of the hydrocarbon feed, where the volume of molecular hydrogen and hydrocarbon feed are based on a temperature of 25° C. and a pressure of 101 kilopascals-absolute, the transition metal element in the catalyst particles can be fed into the separation zone or the second separation zone at a feeding rate in a range of from 25 wppm to 1,000 wppm.

The hydrotreating can occur in the separation zone or the second separation zone and can include countercurrent flow or co-current flow of the hydrocarbon feed relative to the catalyst particles. Similarly, the hydrotreating can include countercurrent flow or co-current flow of the hydrocarbon feed relative to the molecular hydrogen. In certain embodiments, the countercurrent flow can include molecular hydrogen flowing upward through the separation zone or the second separation zone and the hydrocarbon feed and catalyst particles flowing downward through the separation zone.

In certain embodiments, before introducing the hydrocarbon feed or first liquid phase hydrocarbon stream, molecular hydrogen, and catalyst particles into the separation zone or the second separation zone, the hydrocarbon feed or first liquid phase hydrocarbon stream can be mixed with the molecular hydrogen and the catalyst particles and heated to a reaction temperature in a furnace or preheater, e.g., the convection section of a steam cracker. In certain other embodiments, before introducing the hydrocarbon feed or first liquid phase hydrocarbon stream, molecular hydrogen, and catalyst particles into the separation zone or the second separation zone, the hydrocarbon feed or first liquid phase hydrocarbon stream can be heated to a reaction temperature in a furnace or preheater, e.g., the convection section of a steam cracker, the molecular hydrogen and catalyst particles, optionally preheated, can be introduced separately into the separation zone. For example, the hydrocarbon feed or the first liquid phase hydrocarbon and the catalyst particles can be fed into the separation zone or the second separation zone at location(s) above the location at which the molecular hydrogen can be fed into the separation zone or the second separation zone. In another example, the hydrocarbon feed or first liquid phase hydrocarbon stream can be fed into the separation zone or the second separation zone at location(s) above the location at which the molecular hydrogen and catalyst particles can be fed into the separation zone or the second separation zone.

The hydrotreating of the hydrocarbon feed or the first liquid phase hydrocarbon stream can be carried out under conditions that reduce or minimize the amount of any aromatic rings in the hydrocarbon feed that become saturated, reduce or minimize the amount of any sulfur in the hydrocarbon feed that converts into $H_2S$, and/or reduces or minimizes that amount of any nitrogen in the hydrocarbon feed that converts into $NH_3$ within the separation zone or the second separation zone. In certain embodiments, ≤12%, ≤10%, ≤8%, ≤7%, ≤6%, ≤5%, ≤4%, ≤3%, ≤2%, or ≤1% of any aromatic rings present in the hydrocarbon feed can be saturated in the separation zone or the second separation zone. In certain embodiments, ≤55%, ≤50%, ≤45%, ≤40%, ≤35%, ≤30%, or ≤25% of any sulfur present in the hydrocarbon feed can be converted into $H_2S$ in the separation zone or the second separation zone. In certain embodiments, ≤25%, ≤20%, ≤17%, ≤15%, ≤12%, ≤10%, or ≤7% of any nitrogen present in the hydrocarbon feed can be converted into $NH_3$ in the separation zone or the second separation zone. In certain embodiments, ≤10% of any aromatic rings present in the hydrocarbon feed can be saturated in the separation zone or the second separation zone, ≤50% of any sulfur present in the hydrocarbon feed can be converted into $H_2S$ in the separation zone or the second separation zone, and ≤20% of any nitrogen present in the hydrocarbon feed can be converted into $NH_3$ in the separation zone or the second separation zone. In certain other embodiments, ≤5% of any aromatic rings present in the hydrocarbon feed can be saturated in the separation zone or the second separation zone, ≤40% of any sulfur present in the hydrocarbon feed can be converted into $H_2S$ in the separation zone or the second separation zone, and ≤10% of any nitrogen present in the hydrocarbon feed can be converted into $NH_3$ in the separation zone or the second separation zone.

The vapor phase hydrocarbon stream or a mixture of the first vapor phase hydrocarbon stream and the second vapor phase hydrocarbon stream can include 45 wt % to 80 wt % of hydrocarbons, 20 wt % to about 50 wt % of steam, and about 0.5 wt % to about 5 wt % of molecular hydrogen, based on the combined weight of the hydrocarbons, steam, and molecular hydrogen. In certain embodiments, the vapor phase hydrocarbon stream or a mixture of the first vapor phase hydrocarbon stream and the second vapor phase hydrocarbon stream can include at least 0.5 wt %, at least 1 wt %, at least 2 wt %, or at least 3 wt % of the molecular hydrogen, based on the combined weight of the hydrocarbons, steam, and molecular hydrogen.

The separation zone, the first separation zone, and the second separation zone can be or can include, but are not limited to, an internal volume or a portion thereof in one or more vapor-liquid separation stages. In certain embodiments, the vapor-liquid separation stage can include one or more flashing drums or vaporization drums or a portion thereof. In certain embodiments, the vapor-liquid separation stage can be or can include a one-stage flashing vessel with or without reflux. In certain embodiments, the vapor-liquid separation stage can be or can include a one-stage flashing vessel with or without internal structures, e.g., packing. In certain embodiments, the vapor-liquid separation stage can be or can include a one-stage flashing vessel with or without reflux having an open internal separation zone within which the hydrocarbon feed can flow counter-currently through with respect to the molecular hydrogen. When the system includes the first separation zone and the second separation zone, the first and second separation zones can be the same or similar flashing drums or vaporization drums. In certain embodiments, when the system includes the first separation zone and the second separation zone, the first and second separation zones can be similar, but the second separation zone can be larger in size to provide additional residence time for the first liquid phase hydrocarbon stream to contact the molecular hydrogen in the presence of the catalyst particles. Suitable vapor-liquid separation stages in which the first separation zone and/or the second separation zone can be located can include the equipment, e.g., flashing drums, k-pots, slurry reactors, and/or other vapor-liquid separators, disclosed in U.S. Pat. Nos. 3,617,493; 6,632,351; 7,097,758; 7,138,047; 7,220,887; 7,235,705; 7,244,871; 7,247,765; 7,297,833; 7,311,746; 7,312,371; 7,351,872; 7,488,459; 7,578,929; 7,820,035; 7,993,435; 8,105,479; and 9,777,227 and U.S. Patent Application Publication No. 2002/0112987.

In certain embodiments, the internal volume of the separation zone can be an empty or substantially empty. In certain other embodiments, the internal volume of the separation vessel can include one or more structures. Suitable structures can include, but are not limited to, one or more trays, one or more packing materials, or a combination thereof. Illustrative trays can include, but are not limited to, perforated trays, sieve trays, dual flow trays, shower deck trays, disc and donut trays, slit tray, or any combination thereof. The packing material can include, but are not limited to, one or more types of structured and/or random shaped material disposed within the separation zone. The packing material can be made of any suitable material such as metals, polymers, ceramics, glasses, or any combination thereof. Illustrative examples of commercially available random packing material can include, but is not limited to, IMTP®, INTALOX® ULTRA Raschig rings, A-Pak Rings, Saddle Rings, Nutter Rings™, I-Rings™, C-Rings™, P-Rings™, R-Rings™, or any combination thereof. Illustrative examples of commercially available structured packing can include, but is not limited to, corrugated sheets, crimped sheets, gauzes, grids, wire mesh, monolith honeycomb structures, or any combination thereof. For example, suitable structured packing can include, but is not limited to, FLEXIPAC®, FLEXIPAC®, HC®, INTERLOX®, Montz-Pak, MELLAPAK®, mellapakplus, GT-Pak, GT-OPTIM™ PAK, etc.

The catalyst particles can be or can include any suitable transition metal element. Suitable transition metal elements can be or can include, but are not limited to, vanadium, iron, cobalt, nickel, molybdenum, tungsten, and mixtures and combinations thereof. In certain embodiments, the catalyst particles can include a sulfide of the transition metal element. For example, the catalyst particles can be or can include, but are not limited to, a sulfide of vanadium, a sulfide of iron, a sulfide of cobalt, a sulfide of nickel, a sulfide of molybdenum, a sulfide of tungsten, and mixture and combinations thereof.

In certain embodiments, the catalyst particles can be supported catalysts particles. The support can be or can include, but is not limited to, inorganic refractory oxides such as silica, alumina, and mixtures thereof, carbon and mixtures of carbon and inorganic refractory oxides. In certain embodiments, the support can be or can include, but is not limited to, silica, alumina, titania, zirconia, magnesia, pumice, ash, clay, diatomaceous earth, bauxite, spent fluidized catalytic cracker catalyst, or any mixture or combination thereof. In certain embodiments, the catalyst particles can have an average diameter in a range of from 0.5 µm, 5 µm, 10 µm, 20 µm, or 30 µm to 50 µm, 70 µm, 90 µm, or 100 µm.

In certain embodiments, the catalyst particles can be a supported sulfided material prepared from a precursor represented by the formula: $X_bY_c$, where X is a Group 8, 9, or 10 non-noble metal and Y is a Group 8, 9, or 10 non noble metal or a Group 6 metal. The molar ratio of b to c can be in a range of from 0.1:1 to 0.2:1, 0.25:1, 0.35:1, 0.4:1, or 0.5:1 to 0.7:1, 1:1, 1.5:1, 2:1, 2.5:1, or 3:1. In certain other embodiments, the sulfided catalyst particles can include three or more metals, where at least one of the metals can be a Group 8, 9, or 10 non-noble metal and at least one of the metals can be a Group 6 metal where the ratio of the Group 6 metal to Group 8, 9, or 10 non-noble metal can be in a range of from 10:1 to 1:10, supported on an inorganic oxide. In certain other embodiments, the catalyst particles can be supported sulfided metallic catalyst particles that can have a precursor represented by the formula: $X_bMo_cW_dO_z$, where X is a non-noble Group 8, 9, or 10 metal, and a molar ratio of b to (c+d) can be in a range of from 0.1:11 to 3:1; the molar ratio of c to d can be in greater than or equal to 0.01:1, and z can equal $[2b+6(c+d)]2$. In another example, the Group 8, 9, or 10 non-noble metal can be from Ni, Co, or a mixture thereof. In another example, the Group 8, 9, or 10 metal can be Ni, and the X-ray diffraction pattern of the catalyst can be essentially amorphous with crystalline peaks at d equal to 2.53 Angstroms and d equal to 1.70 Angstroms. In another example, the molar ratio of b to (c+d) can be in a range of from 0.25:1 to 2:1 and the molar ratio of c to d can be in a range of from 1:10 to 10:1.

In certain embodiments, the catalyst particles can be prepared by feeding a catalyst precursor that can include the transition metal element, molecular hydrogen, and a sulfur source, e.g., hydrogen sulfide ($H_2S$), into a catalyst production vessel and forming the catalyst particles that include the sulfide of the transition metal element in the catalyst production vessel. The catalyst precursor, molecular hydrogen, and sulfur source can be contacted within the catalyst production vessel under a pressure in a range of from 650 kilopascal-gauge to 13.8 megapascals-gauge. The catalyst precursor, molecular hydrogen, and sulfur source can be contacted within the catalyst production vessel at a temperature in a range of from 200° C., 260° C., or 315° C. to 450° C., 480° C., or 570° C. The catalyst precursor, molecular hydrogen, and sulfur source can be contacted within the catalyst production vessel for a period of time in a range of from 5 minutes, 10 minutes, or 30 minutes to 1 hour, 3 hours, or 4 hours. In certain embodiments, the catalyst particles can be produced according to the process disclosed in WO Publication No. WO 00/42127.

In certain embodiments, the catalyst particles can be prepared by crushing commercially available catalysts and catalyst supports to obtain the desired average catalyst diameter. Without wishing to be bound by theory, it is believed that the selection and control of the particle size distribution of the catalyst can enhance the solid-liquid separation and significantly improve the hydrotreating process. The preparation of the catalyst particles provide control of the particle hardness and attrition resistance, intrinsic catalyst activity, and other catalyst properties that can affect the process performance and physical separation.

The catalyst particles can have a median pore diameter in a range of from 5 nm, 10 nm, 15 nm, or 20 nm to 25 nm, 30 nm, 35 nm, or 40 nm. In certain embodiments, the catalyst particles can have a median pore diameter in a range of from 10 nm to 35 nm, 12 nm to 20 nm, 14 nm to 18 nm, 30 nm to 40 nm, 25 nm to 35 nm, or 30 nm to 35 nm. The median pore diameter of the catalyst particles scan be measured by Hg porosimetry, according to methods well-known in the art. In certain embodiments, the catalyst particles can be or can include the catalyst particles disclosed in U.S. Patent Application Publication no. 2002/0112987.

Pyrolysis

The vapor phase hydrocarbon stream or the first and second vapor phase hydrocarbon streams can be introduced into a pyrolysis reactor, e.g., a steam cracker, and thermally cracked to produce a pyrolysis effluent. In certain embodiments, the pyrolysis reactor can be or can include one or more steam crackers. Suitable steam cracking conditions can include, but are not limited to, one or more of: exposing the vapor phase hydrocarbon stream obtained from the separation zone to a temperature (as measured at a radiant outlet of a steam cracking apparatus) of ≥400° C., e.g., a temperature of about 700° C., about 800° C., or about 900° C. to about 950° C., a pressure of about 0.1 bar to about 5 bars (absolute), and/or a steam cracking residence time of about 0.01 seconds to about 5 seconds. In certain embodiments, the vapor phase hydrocarbon stream or the first and second vapor phase hydrocarbon streams can be steam cracked according to the processes and systems disclosed in U.S. Pat. Nos. 6,419,885; 7,993,435; 9,637,694; and 9,777,227; U.S. Patent Application Publication No. 2018/0170832; and International Patent Application Publication No. WO 2018/111574.

The pyrolysis effluent can be at a temperature of ≥300° C., ≥400° C., ≥500° C., ≥600° C., or ≥700° C., or ≥800° C., or more. The pyrolysis effluent can be cooled via direct contact with a quench medium, indirect heat exchange with a quench medium, or a combination thereof. In certain embodiments, the pyrolysis effluent can be directly contacted with one or more quench mediums to produce a cooled or first cooled effluent. In certain embodiments, the quench medium that can be directly contacted with the pyrolysis effluent can be or can include the liquid phase hydrocarbon stream obtained from the separation zone. In certain other embodiments, the quench medium can be or can include a recycled quench oil separated from the pyrolysis effluent in a primary fractionator. In still certain other embodiments, the quench medium can be the same or similar to the utility fluids disclosed in U.S. Pat. Nos. 9,090,836; 9,637,694; and 9,777,227; and International Patent Application Publication No. WO 2018/111574. The amount of quench medium contacted with the pyrolysis effluent can vary considerably from facility to facility, but the quench medium to pyrolysis effluent weight ratio is typically in the range of about 0.1:1 to about 10:1, e.g., about 0.5:1 to about 5:1, such as about 1:1 to about 4:1.

In certain embodiments, the pyrolysis effluent or the first cooled pyrolysis effluent can be cooled via indirect heat exchange, e.g., boiler feed water, to produce a cooled or second cooled effluent. The cooled pyrolysis effluent can be at a temperature of greater than 150° C., e.g., about 155° C. to about 350° C. The cooled pyrolysis effluent can be introduced into one or more separators, e.g., a tar knock out drum, to separate a bottoms or tar product and an overhead or light product that can be discharged therefrom. In certain embodiments, suitable separation stages can include those disclosed in U.S. Pat. No. 8,083,931. The light product can be at a temperature of about 155° C., about 175° C., about 200° C., or about 225° C. to a about 250° C., about 270° C., about 290° C., about 300° C., or about 315° C. In certain embodiments, the light product can be at a temperature of 155° C. to 315° C., e.g., 250° C. to 315° C. The tar product can have a final atmospheric boiling point of greater than 600° C., as measured according to ASTM D2887-18.

In certain embodiments, at least a portion of the tar product can be mixed, blended, or otherwise combined with the liquid phase hydrocarbon stream or the second liquid phase hydrocarbon stream obtained from the separation zone or the second separation zone, respectively, to produce a bottoms mixture. The first liquid phase hydrocarbon stream, the second liquid phase hydrocarbon stream, or the bottoms mixture can be introduced into a hydroprocessing zone to produce a hydroprocessed product.

In certain embodiments prior to introducing the liquid phase hydrocarbon stream or the second liquid phase hydrocarbon stream into the hydroprocessing zone, at least a portion of the catalyst particles can be separated therefrom. The catalyst particles can be separated from the liquid phase hydrocarbon stream or the second liquid phase hydrocarbon stream via centrifugation, sedimentation or gravity settling, filtering, or any other suitable separator or combination of separators. In certain embodiments, separating at least a portion of the catalyst particles from the liquid phase hydrocarbon stream or the second liquid phase hydrocarbon stream can be accomplished by a cross-flow filtering step integrated with a pump around loop in the separation zone. In the cross-flow filtration zone there can be minimal build-up of filter cake, which can reduce or minimize problems associated with filter binding.

In certain embodiments, the performance of a cross-flow filtering step, if used, can be improved by the use of filter media aids. These filter media aids can be specially sized particles in the size range of from 5 μm to 200 μm that can be used to pre-coat the filter media surface to enhance filter performance Filter design can include a back-flushed and/or a continuously purged configuration. The cross-flow filtration step, if used, can be either close coupled to the separation zone or the second separation zone in an external pump around loop or integrated into the separation zone or the second separation zone design as a section of the separator in combination with a pump around zone.

In certain embodiments, it can be desirable to separate substantially all of the catalyst particles from the liquid phase hydrocarbon stream. As such, the separation step can be carried out under conditions that can increase or maximize the separation of the catalyst particles to produce a recyclable active catalyst product that can be pumped or otherwise conveyed to the hydrocarbon feed and/or into the separation zone or the second separation zone. In certain embodiments, the catalyst particles, preparation thereof, separation thereof from the first liquid phase hydrocarbon stream or the second liquid phase hydrocarbon stream can include the catalyst particles, preparation procedures, and separation processes and systems disclosed in U.S. Patent Application Publication No. 2002/0112987.

The tar product and/or the liquid phase hydrocarbon stream or the second liquid phase hydrocarbon stream can be hydroprocessed in the hydroprocessing zone in the presence of molecular hydrogen and a catalyst under hydroprocessing conditions sufficient to produce a hydroprocessed product having one or more desired properties, e.g., a sufficiently reduced sulfur content. In certain embodiments, a hydrotreated quench oil or hydrocarbon fuel oil stream and a mid-cut solvent can be separated or otherwise obtained from the hydroprocessed product. The quench oil or hydrocarbon fuel oil stream can include less than 5,000 wppm of sulfur, less than 4,500 wppm of sulfur, less than 4,000 wppm of sulfur, or less than 3,500 wppm of sulfur. Illustrative processes and systems that can be used to hydroprocess the tar product and/or the liquid phase hydrocarbon stream can include those disclosed in U.S. Pat. Nos. 9,090,836; 9,206,363; 9,637,694; and 9,777,227; U.S. Patent Application Publication No. 2018/0057759; and International Patent Application Publication No. WO 2018/111574.

In certain embodiments, the mid-cut solvent separated from the hydroprocessed product can be used as a quench medium to further cool the overhead obtained from the separator, e.g., tar knock-out drum, and/or recycled and used a solvent for the liquid phase hydrocarbon stream and/or the tar product during hydroprocessing. The mid-cut solvent can include partially hydrogenated 2-4 ring molecules, e.g., dihydroanthracene and/or tetralin. The partially hydrogenated 2-4 ring molecules can transfer hydrogen radicals to reactive free radicals that can be present in the steam cracker effluent to produce a more stable product.

Returning to the pyrolysis effluent, the pyrolysis effluent can include, but is not limited to, molecular hydrogen, olefins, e.g., ethylene, propylene, and/or one or more butenes, aromatics, e.g., benzene, toluene, and/or xylene, naphtha, gas oil, a heavy oil, and tar. The naphtha, gas oil, heavy oil, and tar each include a mixture of compounds, primarily a mixture of hydrocarbon compounds. The cooled pyrolysis effluent can be introduced into one or more primary fractionators and one or more products can be separated and obtained therefrom.

It should be understood that typically there is an overlap between naphtha and gas oil, an overlap between gas oil and heavy oil or quench oil, and an overlap between heavy oil and tar in composition and boiling point range. Naphtha, also referred to as pygas, is a complex mixture of $C_{5+}$ hydrocarbons, e.g., $C_5$-$C_{10+}$ hydrocarbons, having an initial atmospheric boiling point of 25° C. to 50° C. and a final boiling point of 220° C. to 265° C., as measured according to ASTM D2887-18. In certain embodiments, naphtha can have an initial atmospheric boiling point of 33° C. to 43° C. and a final atmospheric boiling point of 234° C. to 244° C., as measured according to ASTM D2887-18. The final atmospheric boiling point of the gas oil is typically 275° C. to 285° C., as measured according to ASTM D2887-18. The final atmospheric boiling point of the heavy oil or quench oil is typically 455° C. to 475° C., as measured according to ASTM D2887-18. In certain embodiments, the tar product can have an initial boiling point of at least 200° C. and/or a final atmospheric boiling point of >600° C., as measured according to ASTM D2887-18.

FIG. 1 depicts an illustrative system 100 for converting a petroleum feed in line 107 by pyrolysis, according to one or more embodiments. The system 100 can include one or more catalyst production vessels 103, one or more pyrolysis reactors, e.g., steam crackers, 110, one or more separation stages (six are shown) 120, 130, 140, 180, 190, and 195, one or more heat exchange stages (three are shown) 125, 127, 145, and one or more hydroprocessing stages 160.

In certain embodiments, a catalyst precursor via line 101 and molecular hydrogen and a sulfur source, e.g., $H_2S$, via line 102 can be fed into the catalyst production vessel 103. The catalyst particles can be formed in the catalyst production vessel 103 by contacting the catalyst precursor with the sulfur source under conditions sufficient to produce the catalyst particles. The catalyst precursor in line 101 can include a transition metal element, e.g., vanadium, iron, cobalt, nickel, molybdenum, tungsten, or any mixture and combination thereof and the catalyst particles in line 104 can include a sulfide of the transition metal element.

In certain embodiments, the catalyst precursor can be contacted with the molecular hydrogen and the sulfur source in the catalyst production vessel 103 at a temperature of 200° C. to 570° C. for a residence time of from 5 minutes to 4 hours and under a total pressure in a range of from 650 kilopascal-gauge to 13.8 megapascals-gauge. It should be understood that the catalyst production vessel 103 is an optional component of the system 100 and need not be present. For example, if suitable catalyst particles have already been prepared or otherwise acquired the catalyst production vessel 103 can become an unneeded component.

In certain embodiments, the hydrocarbon feed in line 107, steam in line 108, and the catalyst particles, molecular hydrogen, and any unreacted sulfur source in line 105 can be mixed, blended, or otherwise combined to produce a mixture in line 109. In another embodiment, the hydrocarbon feed via line 107 and the steam via line 108 can be combined to produce the mixture in line 109. In this embodiment, the catalyst particles, molecular hydrogen, and any unreacted sulfur source in line 104 can be introduced via line 106 into the first separation stage, e.g., a first vapor-liquid separator, 120. The mixture in line 109 can be heated within a convection section 111 of the pyrolysis reactor 110 to produce a heated mixture via line 113. The heated mixture in line 113 and, depending on the configuration of the system 100, the catalyst particles, molecular hydrogen, and any unreacted sulfur source via line 106 can be introduced into the first separation stage 120. At least a portion of the hydrocarbon feed and at least a portion of the molecular hydrogen can contact in the presence of the catalyst particles under hydrotreating conditions in a separation zone in the first separation stage 120. The separation zone can include the entire internal volume of the first vapor-liquid separator 120 or just a portion thereof. In certain embodiments, molecular hydrogen via line 114 can be introduced into the first separation stage 120.

In certain embodiments, the hydrocarbon feed and the molecular hydrogen can be contacted in the separation zone under a total pressure of less than 3,500 kilopascals-gauge. The molecular hydrogen can be fed into the first vapor-liquid separator at a rate of no greater than 270 cubic meters of molecular hydrogen per cubic meter of the hydrocarbon feed, where the volume of molecular hydrogen and hydrocarbon feed are based on a temperature of 25° C. and a pressure of 101 kilopascals-absolute. The first separation stage 120 can be sufficiently sized to cause the hydrocarbon feed to contact the molecular hydrogen in the separation zone for a residence time of from 20 minutes to 2 hours. The hydrocarbon feed and molecular hydrogen can be contacted in the separation zone in the first separation stage 120 at a temperature of from 250° C. to 500° C. The transition metal element in the catalyst particles can be fed into the separation zone in first separation stage 120 at a feeding rate in a range of from 50 wppm to 500 wppm, based on the weight of the hydrocarbon feed. In certain embodiments, the hydrocarbon feed and the catalyst particles can be fed into the separation zone in the first separation stage 120 at location (s) above the location(s) at which the molecular hydrogen can be fed into the separation zone in the first separation stage 120. In certain embodiments, the molecular hydrogen can flow counter-current with respect to the hydrocarbon feed and the catalyst particles.

In certain embodiments, the hydrotreating conditions within the separation zone in the first separation stage 120 can be carried out under conditions that reduce or minimize the amount of any aromatic rings in the hydrocarbon feed that become saturated, reduce or minimize the amount of any sulfur in the hydrocarbon feed that becomes converted into $H_2S$, and/or reduce or minimize the amount of any nitrogen in the hydrocarbon feed that becomes converted into $NH_3$ within the separation zone in first separation stage 120. In certain embodiments, ≤10% of any aromatic rings present in the hydrocarbon feed can be saturated in the separation zone in the first separation stage 120, ≤50% of any sulfur present in the hydrocarbon feed can be converted into $H_2S$ in the separation zone in the first separation stage 120, and/or ≤20% of any nitrogen present in the hydrocarbon feed can be converted into $NH_3$ in the separation zone in the first separation stage 120.

A vapor phase hydrocarbon stream via line 121 and a liquid phase hydrocarbon stream via line 122 can be discharged from the first separation stage 120. The vapor phase hydrocarbon stream via line 121 can be heated in the convection section 111 of the pyrolysis reactor 110 to produce a heated vapor phase hydrocarbon stream via line 123. The heated vapor phase hydrocarbon stream via line 123 can be introduced into a radiant section 112 of the pyrolysis reactor 110. The pyrolysis reactor 110 can effect pyrolysis of at least a portion of the first vapor phase hydrocarbon stream to produce a pyrolysis effluent that can discharged via line 124 therefrom.

The pyrolysis effluent in line 124 can be introduced into a quenching section that can quench the pyrolysis effluent to produce a cooled pyrolysis effluent. The quenching section can include one or more heat exchange stages. As shown, the quenching section can include one or more first heat exchangers, e.g., a transfer line exchanger, 125 and one or more second heat exchanges, e.g., an indirect heat exchanger, 127. In certain embodiments, at least a portion of the liquid phase hydrocarbon in line 122 can be used to quench the pyrolysis effluent in the transfer line exchanger 125. As shown, the liquid phase hydrocarbon stream in line 122 can be introduced into the second separation stage, e.g., a solid-liquid separator, 130 to separate out at least a portion of the catalyst particles therefrom. A catalyst-lean liquid phase hydrocarbon stream via line 131 and a catalyst-rich product via line 132 can be discharged from the second separation stage 130. The second separation stage 130 can include, but is not limited to, one or more cyclones or centrifuges, one or more sedimentation or gravity separators, one or more filters, or any combination thereof. In certain embodiments, the catalyst particles via line 132 can be recycled to the first separation stage 120. In certain embodiments, the catalyst particles via line 122 can be recycled to the catalyst production vessel 103. At least a portion of the catalyst-lean liquid phase hydrocarbon stream in line 131 can be introduced via line 133 into the first heat exchanger 125 to produce a first cooled pyrolysis effluent.

The first cooled pyrolysis effluent via line 126 can be discharged from the first heat exchanger and introduced into the second heat exchanger 127. A second or cooled pyrolysis effluent via line 128 can be discharged from the second heat exchanger 127. The cooled pyrolysis effluent can be at a temperature in a range of from 260° C. to 650° C. or greater. The cooled pyrolysis effluent can be introduced into the third separation stage, e.g., a vapor-liquid separator, 140. A bottoms or tar product via line 141 and an overhead or vapor phase via line 142 can be discharged from the third separation stage 140. The overhead via line 142 can be introduced into the third heat exchange stage, e.g., one or more indirect heat exchangers, to produce a cooled overhead that can be discharged via line 146. The cooled overhead can be at a temperature in a range of from 150° C., 165° C., 195° C., or 220° C. to 230° C., 250° C., 270° C., 285° C., or 300° C.

The cooled overhead via line 146 can be introduced into the fourth separation stage, e.g., a vapor-liquid separator such as a primary fractionator, 190. A plurality of products can be separated from the cooled overhead and conducted away from the fourth separation stage 190. Illustrative products that can be separated from the cooled overhead in line 146 within the fourth separation stage 190 and conducted away therefrom can include, but are not limited to, quench oil via line 191, gas oil via line 192, naphtha via line 193, and an overhead via line 194. The overhead via line 194 can be introduced into the fifth separation stage, e.g., a chill train, 195 and various light products such as molecular hydrogen via line 196 and ethylene via line 197 can be separated therefrom. Other product can include, but are not limited to, methane, propylene, ethane, propane, butane, etc. In certain embodiments at least a portion of the quench oil in line 191 can be combined via line 198 with the cooled pyrolysis effluent in line 128 to further cool the pyrolysis effluent. In certain embodiments, at least a portion of the quench oil in line 191 can be removed via line 199 from the system 100.

Returning to the catalyst-lean liquid phase hydrocarbon stream in line 131, molecular hydrogen via line 154 and at least a portion of the catalyst-lean liquid phase hydrocarbon stream in line 131 via line 134 can be introduced into the hydroprocessing stage 160. In certain embodiments, at least a portion of the bottoms or tar product via line 141 can also be introduced into the hydroprocessing stage 160. A hydroprocessed product via line 162 can be discharged from the hydroprocessing stage 160.

The hydroprocessing conditions typically include a temperature of 200° C. or greater; a total pressure 3.5 MPa or greater, e.g., 6 MPa or greater; a weight hourly space velocity of 0.2 $hr^{-1}$ or greater, 0.25 $hr^{-1}$ or greater, or 0.3 $hr^{-1}$ or greater, based on the weight of the catalyst-lean liquid phase hydrocarbon stream and, if present, the tar product that is subjected to the hydroprocessing; and a total amount of molecular hydrogen supplied to the hydroprocessing stage 160 can be 1,000 or greater standard cubic feet per barrel of the catalyst-lean liquid phase hydrocarbon stream and, if present, the tar product that is subjected to the hydroprocessing (178 S $m^3/m^3$). Conditions can be selected within the hydroprocessing conditions to achieve a 566° C.+ conversion of ≥20 wt. % substantially continuously for at least ten days at a molecular hydrogen consumption rate of about 2,200 standard cubic feet per barrel of the catalyst-lean liquid phase hydrocarbon stream and, if present, the tar product that is subjected to the hydroprocessing 123 (SCF/B) (392 S $m^3/m^3$) to 3,200 SCF/B (570 S $m^3/m^3$). In certain embodiments, the hydroprocessing conditions can be the same or similar to the hydroprocessing conditions, e.g., the intermediate hydroprocessing conditions, disclosed in WO Publication No. WO2018/111574.

The hydroprocessed product via line 162 can be introduced into the sixth separation stage, e.g., a vapor-liquid separator, 180. In certain embodiments, a hydrotreated quench oil or hydrocarbon fuel oil stream via line 181, a mid-cut solvent via line 182, and molecular hydrogen via line 183 can be discharged from the sixth separation stage 180. As shown, in certain embodiments, at least a portion of the mid-cut solvent via line 184 can be combined with the cooled overhead in line 146 prior to introducing the cooled overhead via line 146 into the fourth separation stage 190 and/or with the catalyst-lean liquid phase hydrocarbon stream in line 134 prior to introduction into the hydroprocessing stage 160. In certain embodiments, at least a portion of the mid-cut solvent via line 185 can be removed from the system 100. In certain embodiments, at least a portion of the hydrotreated quench oil via line 186 can be combined with the heated mixture in line 113 and introduced into the first separation stage 120. In certain embodiments, at least a portion of the hydrotreated quench oil via line 187 can be removed from the system 100.

The hydrotreated quench oil in line 181 can include hydroprocessed tar that can include partially saturated polyaromatic rings having a boiling range of 350° C. to 650° C. or more. The mid-cut solvent in line 182 can include partially hydrogenated 2-4 ring molecules, e.g., dihydroanthracene and tetralin. The partially hydrogenated 2-4 ring molecules can transfer hydrogen radicals to reactive free radicals in the steam cracker effluent to produce a more stable product.

Figure 2:
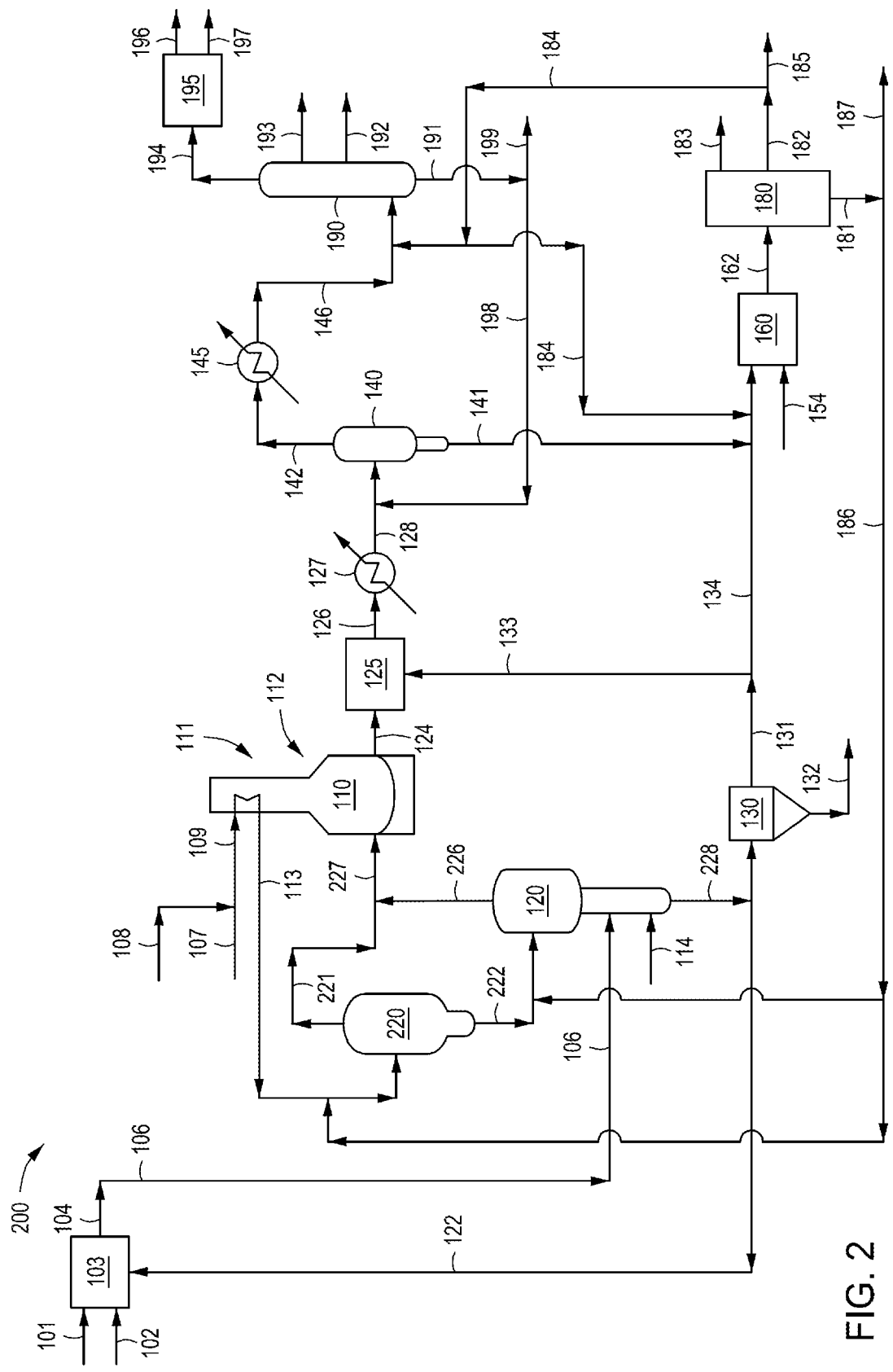
FIG. 2 depicts another illustrative system for converting a petroleum feed by pyrolysis, according to one or more embodiments described.

FIG. 2 depicts another illustrative system for converting a petroleum feed by pyrolysis, according to one or more embodiments. The system 200 is similar to the system 100, but can further include one or more additional separation stages, e.g., a vapor-liquid separator, 220. As such, the system 200 can include, but is not limited to, the separation stages 120, 130, 140, 180, 190, 195, and 220. The separation stages shown in FIG. 2 can be referred to as the first, second, third, fourth, fifth, sixth, and seventh separation stage 220, 120, 130, 140, 190, 195, and 180, respectively. The addition of the first separation stage 220 can be used in combination with the second separation state 120 to facilitate separation of the heated mixture in line 113 into a vapor phase and a liquid phase.

In certain embodiments, the first separation stage 220 can be or can include a one-stage flashing vessel with or without reflux. In certain embodiments, the first separation stage 220 can be or can include a one-stage flashing vessel with or without internal structures, e.g., packing. In certain embodiments, the first separation stage 220 can be or can include a one-stage flashing vessel with or without reflux having an open internal separation zone within which the hydrocarbon feed can separate into a vapor phase portion and a liquid phase portion. Suitable separation stages can include the flashing drums disclosed in U.S. Pat. Nos. 3,617,493; 7,138, 047; 7,674,366; 7,718,049; 7,993,435; 8,105,479; and 9,777,227.

As shown in FIG. 2, the hydrocarbon feed via line 107 and steam via line 108 can be mixed to produce the mixture in line 109 that can be heated in the convection section 111 of the pyrolysis furnace 110. The heated mixture via line 113 can be introduced into the first separation stage 220 and a first vapor phase hydrocarbon stream via line 221 and a first liquid phase hydrocarbon via line 222 can be discharged therefrom. The first liquid phase hydrocarbon stream via line 222, the catalyst particles, molecular hydrogen, and any hydrogen source discharged via line 104 from the catalyst production vessel 103, and optionally additional molecular hydrogen via line 114 can be introduced into the second separation stage 120. The first liquid phase hydrocarbon stream can contact the molecular hydrogen in the presence of the catalyst particles under hydrotreating conditions in the second separation zone in the second separation stage 120.

In certain embodiments, the hydrotreating conditions in the second separation zone in the second separation stage 120 can be carried out under conditions that reduce or minimize the amount of any aromatic rings in the hydrocarbon feed that become saturated, reduce or minimize the amount of any sulfur in the hydrocarbon feed that becomes converted into $H_2S$, and/or reduce or minimize the amount of any nitrogen in the hydrocarbon feed that becomes converted into $NH_3$ in the second separation zone. In certain embodiments, ≤10% of any aromatic rings present in the first liquid phase hydrocarbon stream can be saturated in the second separation zone, ≤50% of any sulfur present in the first liquid phase hydrocarbon stream can be converted into $H_2S$ in the second separation zone, and/or ≤20% of any nitrogen present in the second liquid phase hydrocarbon stream can be converted into $NH_3$ in the second separation zone.

A second vapor phase hydrocarbon stream via line 226 and a second liquid phase hydrocarbon stream via line 228 can be discharged from the second vapor-liquid separation stage 120. The first vapor phase hydrocarbon stream in line 221 and the second vapor phase hydrocarbon stream in line 226 can be mixed, blended, or otherwise combined to produce a mixed vapor phase hydrocarbon stream in line 227. The mixed vapor phase hydrocarbon stream can be introduced into the radiant section of 112 of the pyrolysis furnace 110 and the pyrolysis effluent can be discharged via line 124 therefrom.

Example

The foregoing discussion can be further described with reference to the following non-limiting prophetic example.

The increase in the amount of the vapor phase hydrocarbon stream recovered from the separation zone was estimated via a combination of experiments and simulation. Using the data generated from low pressure, low conversion hydrocracking experiments, a simple hydrocracking model was constructed and applied to this disclosure. Table 1 shows the data used to fit the hydrocracking model. Table 2 shows the material balance for a comparative case and inventive case each feeding 1,066 T/hr of Arab Light Crude Oil and producing 146 T/hr (1,200 KTA) of ethylene. In the inventive example, for the same ethylene production rate, the crude feed rate was reduced to 882 T/hr (a 17% reduction).

TABLE 1

| | Boiling Range (° F.) | | | | | | | |
|---|---|---|---|---|---|---|---|---|
| | <10 | 10-80 | 80-150 | 150-320 | 320-500 | 500-700 | 700-1,000 | 1000+ |
| Boiling Cut | Fuel Gas | C4s | Light Naphtha | Heavy Naptha | Jet Fuel | Distillate | Vacuum Gas Oil | Residum |
| Exp. Data | 3.5% | 0.3% | 3.7% | 21.2% | 9.0% | 18.8% | 31.9% | 11.7% |
| Model Prediction | 7.6% | 3.1% | 4.6% | 8.0% | 6.4% | 14.9% | 49.5% | 5.8% |

The comparative case utilizes 50 wt % steam as a diluent to the pyrolysis. The flow rate of steam into the steam cracker in the comparative case is 768 T/hr. For this disclosure, the total molar rate of diluent was kept constant. Furthermore, it was assumed that hydrogen is equally effective as a diluent as steam. The unconverted hydrogen coming from the separation zone (3.1 T/hr) is able to displace 27.8 T/hr of steam to achieve the same molar flow rate of diluent into the steam cracker. The hydrogen from the separation zone makes up 3.6% of the total steam+hydrogen diluent to the steam cracker on a molar basis.

Most of the steam diluent condenses in the quench zone after pyrolysis and before the process gas compressor (PGC). The hydrogen diluent from the separation zone does not condense and, therefore, increases the volumetric flow rate to the PGC. The volumetric flow rate through the PGC increases from 310 to 344 $Mm^3$/hr, equivalent to an 11% increase. The mass flow rate through the PGC, however, increases from 456 T/hr to 458 T/hr, for an increase of only 0.4%. This small change in mass flow is due to the low molecular weight of hydrogen. While the size of the piping and compressor are proportional to the volumetric gas flow, the shaft power needed to drive the compressor is more closely related to the mass flow. The configuration utilizes a first vapor-liquid separation stage and a second vapor-liquid separation stage as shown in FIG. 2. The transition metal element is sulfide molybdenum on carbon (MoS2/C), and the catalyst is introduced into the second separation stage at a feed rate of 200 wpppm, based on the weight of the hydrocarbon feed.

TABLE 2

(weight % basis)

|  | Comparative | Inventive |
|---|---|---|
| Desalted Crude | 100 | 100 |
| $H_2$ to Separation Zone | 0 | 0.8 |
| First Separation Stage Overhead | 72.1 | 72.1 |
| First Separation Stage Bottoms | 27.9 | 27.9 |
| Second Separation Stage Overhead | 0 | 16.2 |
| Second Separation Stage Bottoms | 0 | 12.6 |
| Primary Fractionator Overhead | 42.8 | 52 |
| Ethylene Product | 13.7 | 16.5 |

One of the main attributes that determines the quality of a feed to a steam cracker is the hydrogen content of the feed. Generally, a hydrogen content greater than 12.5 wt % is desired. In the comparative case, the hydrogen content of the vapor to pyrolysis is 13.7 wt %. With this disclosure, the hydrogen content of the vapor phase hydrocarbon stream obtained from the separation zone (excluding molecular hydrogen) is 13.1 wt %, and the combined feed to pyrolysis is 13.6% wt % hydrogen. This is a very small reduction in the hydrogen content, and still well above the 12.5% guideline.

As can be seen from the data in Table 2, by employing the second separation stage in which at least a portion of the hydrocarbon feed and at least a portion of the molecular hydrogen is contacted in the presence of the catalyst particles, the amount of ethylene produced surprisingly and unexpectedly increased by 20.4%.

Listing of Embodiments

This disclosure may further include the following non-limiting embodiments.

A1. A process for converting a hydrocarbon feed by pyrolysis, comprising: (I) feeding the hydrocarbon feed, a plurality of catalyst particles, and molecular hydrogen into a separation zone, wherein the catalyst particles comprise a transition metal element; (II) contacting at least a portion of the hydrocarbon feed and at least a portion of the molecular hydrogen in the presence of the catalyst particles under hydrotreating conditions in the separation zone, wherein the hydrocarbon feed and the molecular hydrogen are contacted under a total pressure of less than 3,500 kilopascals-gauge, and wherein the molecular hydrogen is fed into the separation zone at a rate of no greater than 270 cubic meters of molecular hydrogen per cubic meter of the hydrocarbon feed, wherein the volume of molecular hydrogen and hydrocarbon feed are based on a temperature of 25° C. and a pressure of 101 kilopascals-absolute; (III) obtaining from the separation zone a vapor phase hydrocarbon stream and a liquid phase hydrocarbon stream; and (IV) feeding at least a portion of the vapor phase hydrocarbon stream into a pyrolysis reaction zone to produce a pyrolysis effluent comprising olefins and molecular hydrogen.

A2. The process of A1, wherein the hydrocarbon feed and the molecular hydrogen are contacted in step (II) under a total pressure in the separation zone in a range of from 650 kilopascals-gauge to 1,750 kilopascals-gauge.

A3. The process of A1 or A2, wherein the molecular hydrogen is fed into the separation zone at a rate of 36 $m^3$ to 180 $m^3$ of molecular hydrogen per cubic meter of the hydrocarbon feed.

A4. The process of any of A1 to A3, wherein the hydrocarbon feed and the molecular hydrogen are contacted in step (II) at a temperature in the separation zone of from 250° C. to 500° C.

A5. The process of any of A1 to A4, wherein the hydrocarbon feed and the molecular hydrogen are contacted in step (II) at a temperature in the separation zone of from 400° C. to 500° C.

A6. The process of any of A1 to A5, wherein the hydrocarbon feed and the molecular hydrogen are contacted in step (II) for a residence time of from 20 minutes to 2 hours.

A7. The process of any of A1 to A6, wherein the transition metal element is selected from vanadium, iron, cobalt, nickel, molybdenum, tungsten, and mixtures and combinations thereof.

A8. The process of any of A1 to A7, wherein the catalyst particles comprise a sulfide of the transition metal element.

A9. The process of any of A1 to A8, wherein the transition metal element in the catalyst particles is fed into the separation zone at a feeding rate in a range of from 50 wppm to 500 wppm, based on the weight of the hydrocarbon feed.

A10. The process of any of A1 to A9, wherein the transition metal element in the catalyst particles is fed into the separation zone at a feeding rate in a range of from 75 wppm to 250 wppm, based on the weight of the hydrocarbon feed.

A11. The process of any of A1 to A10, wherein the hydrocarbon feed and the catalyst particles are fed into the separation zone at location(s) above the location at which the molecular hydrogen is fed into the separation zone.

A12. The process of any of A1 to A11, wherein the hydrocarbon feed comprises a resid.

A13. The process of any of A1 to A12, wherein the hydrocarbon feed comprises one or more plastic materials.

A14. The process of any of A1 to A13, wherein the hydrocarbon feed comprises crude oil or a fraction thereof and one or more plastic materials.

A15. The process of A14, wherein the hydrocarbon feed comprises from 1 wt % to 40 wt % of the one or more plastic materials based on the total weight of the hydrocarbon feed.

A16. The process of any of A1 to A15, wherein ≤10% of any aromatic rings present in the hydrocarbon feed are saturated in the separation zone.

A17. The process of any of A1 to A16, wherein ≤5% of any aromatic rings present in the hydrocarbon feed are saturated in the separation zone.

A18. The process of any of A1 to A17, wherein ≤50% of any sulfur present in the hydrocarbon feed is converted into $H_2S$ in the separation zone.

A19. The process of any of A1 to A18, wherein ≤40% of any sulfur present in the hydrocarbon feed is converted into $H_2S$ in the separation zone.

A20. The process of any of A1 to A19, wherein ≤20% of any nitrogen present in the hydrocarbon feed is converted into $NH_3$ in the separation zone.

A21. The process of any of A1 to A20, wherein ≤10% of any nitrogen present in the hydrocarbon feed is converted into $NH_3$ in the separation zone.

A22. The process of any of A1 to A21, wherein the separation zone is a flashing drum, or a portion thereof.

A23. The process of any of A1 to A22, further comprising: feeding a catalyst precursor and a sulfur source compound into a catalyst production vessel; and forming the catalyst particles comprising a sulfide of the transition metal element in the catalyst production vessel.

A24. The process of any of A1 to A23, further comprising: obtaining from the pyrolysis effluent a pyrolysis tar stream; and feeding the pyrolysis tar stream and at least a portion of the liquid phase hydrocarbon stream into a hydroprocessing zone to produce a hydrocarbon fuel oil stream comprising less than 5,000 wppm of sulfur.

A25. The process of A24, further comprising removing solid particles from the liquid phase hydrocarbon stream before feeding the at least a portion of the liquid phase hydrocarbon stream into the hydroprocessing zone.

A26. The process of A24 or A25, further comprising: obtaining from the hydrocarbon fuel oil stream a mid-distillate stream; and recycling at least a portion of the mid-distillate stream to the hydroprocessing zone as a solvent.

A27. The process of any of A1 to A26, wherein contacting the hydrocarbon feed with the molecular hydrogen in the presence of the catalyst particles in the separation zone increases an amount of the vapor phase hydrocarbon stream recovered from the separation zone by at least 5 wt %, at least 10 wt %, at least 15 wt %, or at least 20 wt %, as compared to introducing the hydrocarbon feed into the separation zone in the absence of the molecular hydrogen and in the absence of the catalyst particles.

A28. The process of any of A1 to A27, wherein contacting the hydrocarbon feed with the molecular hydrogen in the presence of the catalyst particles in the separation zone increases an amount of overhead vapor recovered from a primary fractionator separating a pyrolysis effluent produced by pyrolyzing the vapor phase hydrocarbon stream obtained from the separation zone by at least 5 wt %, at least 10 wt %, at least 15 wt %, or at least 20 wt %, as compared to introducing the hydrocarbon feed into the separation zone in the absence of the molecular hydrogen and in the absence of the catalyst particles.

B1. A process for converting a hydrocarbon feed by pyrolysis, comprising: (I) heating a hydrocarbon feed to produce a heated hydrocarbon feed comprising a vapor phase and a liquid phase; (II) feeding the heated hydrocarbon feed into a first separation zone; (III) obtaining from the first separation zone a first vapor phase hydrocarbon stream and a first liquid phase hydrocarbon stream; (IV) feeding the first liquid phase hydrocarbon stream, a plurality of catalyst particles, and molecular hydrogen into a second separation zone, wherein the catalyst particles comprise a transition metal element; (V) contacting at least a portion of the first liquid phase hydrocarbon stream and at least a portion of the molecular hydrogen in the presence of the catalyst particles under hydrotreating conditions in the second separation zone, wherein the first liquid phase hydrocarbon and the molecular hydrogen are contacted under a total pressure of less than 3,500 kilopascals-gauge, wherein the molecular hydrogen is fed into the second separation zone at a rate of no greater than 270 cubic meters of molecular hydrogen per cubic meter of the hydrocarbon feed, and wherein the volume of molecular hydrogen and hydrocarbon feed are based on a temperature of 25° C. and a pressure of 101 kilopascals-absolute; (VII) obtaining a second vapor phase hydrocarbon stream and a second liquid phase hydrocarbon stream from the second separation zone; and (VIII) feeding at least a portion of the first vapor phase hydrocarbon stream and at least a portion of the second vapor phase hydrocarbon stream into a pyrolysis reaction zone to produce a pyrolysis effluent comprising olefins and molecular hydrogen.

B2. The process of B1, wherein the first liquid phase hydrocarbon stream and the molecular hydrogen are contacted in step (V) under a total pressure in the second separation zone in a range of from 650 kilopascals-gauge to 1,750 kilopascals-gauge.

B3. The process of claim B1 or B2, wherein the molecular hydrogen is fed into the second separation zone at a rate of 36 m³ to 180 m³ of molecular hydrogen per cubic meter of the hydrocarbon feed.

B4. The process of any of B1 to B3, wherein the first liquid phase hydrocarbon stream and the molecular hydrogen are contacted in step (V) at a temperature in the second separation zone of from 250° C. to 500° C.

B5. The process of any of B1 to B4, wherein the first liquid phase hydrocarbon stream and the molecular hydrogen are contacted in step (V) for a residence time of from 20 minutes to 2 hours.

B6. The process of any of B1 to B5, wherein the transition metal element is selected from vanadium, iron, cobalt, nickel, molybdenum, tungsten, and mixtures and combinations thereof.

B7. The process of any of B1 to B6, wherein the catalyst particles comprise a sulfide of the transition metal element.

B8. The process of any of B1 to B7, wherein the transition metal element in the catalyst particles is fed into the second separation zone at a feeding rate in a range of from 50 wppm to 500 wppm, based on the weight of the first liquid phase hydrocarbon stream.

B9. The process of any of B1 to B8, wherein the hydrocarbon feed comprises a resid.

B10. The process of any of B1 to B9, wherein the hydrocarbon feed comprises one or more plastic materials.

B11. The process of any of B1 to B10, wherein the hydrocarbon feed comprises crude oil or a fraction thereof and one or more plastic materials.

B12. The process of any of B1 to B11, wherein ≤10% of any aromatic rings present in the first liquid phase hydrocarbon stream are saturated in the second separate zone.

B13. The process of any of B1 to B12, wherein ≤5% of any aromatic rings present in the first liquid phase hydrocarbon stream are saturated in the second separate zone.

B14. The process of any of B1 to B13, wherein ≤50% of any sulfur present in the first liquid phase hydrocarbon stream is converted into $H_2S$ in the second separation zone.

B15. The process of any of B1 to B14, wherein ≤40% of any sulfur present in the first liquid phase hydrocarbon stream is converted into $H_2S$ in the second separation zone.

B16. The process of any of B1 to B15, wherein ≤20% of any nitrogen in the first liquid phase hydrocarbon stream is converted into $NH_3$ in the second separation zone.

B17. The process of any of B1 to B16, wherein ≤10% of any nitrogen in the first liquid phase hydrocarbon stream is converted into $NH_3$ in the second separation zone.

B18. The process of any of B1 to B17, wherein the second separation zone is a flashing drum, or a portion thereof.

B19. The process of any of B1 to B18, further comprising: feeding a catalyst precursor and a sulfur source compound into a catalyst production vessel; and forming the catalyst particles comprising a sulfide of the transition metal element in the catalyst production vessel.

B20. The process of any of B1 to B19, further comprising: obtaining from the pyrolysis effluent a pyrolysis tar stream; and feeding the pyrolysis tar stream and at least a portion of the second liquid phase hydrocarbon stream into a hydroprocessing zone to produce a hydrocarbon fuel oil stream comprising less than 5,000 wppm of sulfur.

B21. The process of B20, further comprising removing solid particles from the second liquid phase hydrocarbon stream before feeding the at least a portion of the second liquid phase hydrocarbon stream into the hydroprocessing zone.

B22. The process of B20 or B21, further comprising: obtaining from the hydrocarbon fuel oil stream a mid-distillate stream; and recycling at least a portion of the mid-distillate stream to the hydroprocessing zone as a solvent.

C1. A system for converting a hydrocarbon feed by pyrolysis, the system comprising: (i) a first vapor-liquid separator adapted for receiving a hydrocarbon feed, a plurality of catalyst particles, and molecular hydrogen, allowing at least a portion of the hydrocarbon feed to contact at least a portion of the molecular hydrogen in the presence of the catalyst particles under hydrotreating conditions, discharging a first vapor phase hydrocarbon stream, and discharging a first liquid phase hydrocarbon stream, wherein the catalyst particles comprise a transition metal element, wherein the hydrocarbon feed and the molecular hydrogen are contacted under a total pressure of less than 3,500 kilopascals-gauge, and wherein the molecular hydrogen is fed into the first vapor-liquid separator at a rate of no greater than 270 cubic meters of molecular hydrogen per cubic meter of the hydrocarbon feed, wherein the volume of molecular hydrogen and hydrocarbon feed are based on a temperature of 25° C. and a pressure of 101 kilopascals-absolute; (ii) a pyrolysis reactor adapted for receiving the first vapor phase hydrocarbon stream, heating the first vapor phase hydrocarbon stream to effect pyrolysis of at least a portion of the first vapor phase hydrocarbon stream, and discharging a pyrolysis effluent stream; (iii) a quenching section adapted for receiving the pyrolysis effluent stream, quenching the pyrolysis effluent stream, and discharging a quenched pyrolysis effluent stream; (iv) a second vapor-liquid separator adapted for receiving the quenched pyrolysis effluent stream, separating the quenched pyrolysis effluent stream to obtain a second vapor phase hydrocarbon stream comprising olefins and a second liquid phase hydrocarbon stream comprising pyrolysis tar, discharging the second vapor phase hydrocarbon stream, and discharging the second liquid phase hydrocarbon stream; and (v) a hydroprocessing unit adapted for receiving the first liquid phase hydrocarbon stream and the second liquid phase hydrocarbon stream, hydroprocessing the first liquid phase hydrocarbon stream and the second liquid phase hydrocarbon stream under hydroprocessing conditions to produce a hydrocarbon fuel oil stream comprising less than 5,000 wppm of sulfur, and discharging the hydrocarbon fuel oil stream.

C2. The system of C1, wherein the first vapor-liquid separator comprises a flashing drum.

C3. The system of C1, wherein the first vapor-liquid separator comprises a flashing drum free of any internal structures.

C4. The system of C1, wherein the first vapor-liquid separator comprises a flashing drum, and wherein the flashing drum comprises internal structures disposed therein.

C5. The system of C4, wherein the internal structures comprise one or more trays, one or more packing materials, or a combination thereof.

C6. The system of any of C1 to C5, wherein first vapor-liquid separator is adapted to contact the hydrocarbon feed and the molecular hydrogen under a total pressure in a range of from 650 kilopascals-gauge to 1,750 kilopascals-gauge.

C7. The system of any of C1 to C6, wherein the first vapor-liquid separator is adapted to receive the molecular hydrogen at a rate of 36 $m^3$ to 180 $m^3$ of molecular hydrogen per cubic meter of the hydrocarbon feed.

C8. The system of any of C1 to C7, wherein first vapor-liquid separator is adapted to contact the hydrocarbon feed and the molecular hydrogen at a temperature of from 250° C. to 500° C.

C9. The system of any of C1 to C8, wherein first vapor-liquid separator is adapted to contact the hydrocarbon feed and the molecular hydrogen at a temperature of from 400° C. to 500° C.

C10. The system of any of C1 to C9, wherein first vapor-liquid separator is adapted to contact the hydrocarbon feed and the molecular hydrogen for a residence time of from 20 minutes to 2 hours.

C11. The system of any of C1 to C10, wherein the transition metal element is selected from vanadium, iron, cobalt, nickel, molybdenum, tungsten, and mixtures and combinations thereof.

C12. The system of any of C1 to C11, wherein the catalyst particles comprise a sulfide of the transition metal element.

C13. The system of any of C1 to C12, wherein the first vapor-liquid separator is adapted to receive the transition metal element in the catalyst particles at a feeding rate in a range of from 50 wppm to 500 wppm, based on the weight of the hydrocarbon feed.

C14. The system of any of C1 to C13, wherein the first vapor-liquid separator is adapted to receive the transition metal element in the catalyst particles at a feeding rate in a range of from 75 wppm to 250 wppm, based on the weight of the hydrocarbon feed.

C15. The system of any of C1 to C14, wherein the first vapor-liquid separator is adapted to receive the hydrocarbon feed and the catalyst particles at location(s) above the location at which the molecular hydrogen is adapted to be received.

C16. The system of any of C1 to C15, wherein the hydrocarbon feed comprises a resid.

C17. The system of any of C1 to C16, wherein the hydrocarbon feed comprises one or more plastic materials.

C18. The system of C17, wherein the hydrocarbon feed comprises from 1 wt % to 40 wt % of the one or more plastic materials based on the total weight of the hydrocarbon feed.

C19. The system of any of C1 to C18, wherein ≤10% of any aromatic rings present in the first liquid phase hydrocarbon stream are saturated in the second separate zone.

C20. The system of any of C1 to C19, wherein ≤50% of any sulfur present in the first liquid phase hydrocarbon stream is converted into $H_2S$ in the second separation zone.

C21. The system of any of C1 to C20, wherein ≤20% of any nitrogen in the first liquid phase hydrocarbon stream is converted into $NH_3$ in the second separation zone.

C22. The system of any of C1 to C21, further comprising a catalyst production vessel adapted for receiving a catalyst precursor and a sulfur source compound, forming the catalyst particles therein, and discharging the catalyst particles therefrom, wherein the catalyst particles comprise a sulfide of the transition metal element.

C23. The system of any of C1 to C22, further comprising a solid-liquid separator adapted for separating at least a portion of the catalyst particles from the first liquid phase hydrocarbon stream, discharging a catalyst-lean liquid phase, and discharging a catalyst-rich product.

C24. The system of any of C1 to C23, further comprising a third vapor-liquid separator adapted for receiving the hydrocarbon fuel oil stream, discharging a hydrotreated quench oil, and discharging a mid-cut solvent.

C25. The system of any of C1 to C24, wherein the quenching section comprises a transfer line exchanger, an indirect heat exchanger, or a combination thereof.

D1. A system for converting a hydrocarbon feed by pyrolysis, the system comprising: (i) a first vapor-liquid separator adapted for receiving a hydrocarbon feed, separating the hydrocarbon feed into a first vapor phase hydrocarbon stream and a first liquid phase hydrocarbon stream, discharging the first vapor phase hydrocarbon stream, and discharging the first liquid phase hydrocarbon stream; (ii) a second vapor-liquid separator adapted for receiving the first liquid phase hydrocarbon stream, a plurality of catalyst particles, and molecular hydrogen, allowing at least a portion of the first liquid phase hydrocarbon stream to contact at least a portion of the molecular hydrogen in the presence of the catalyst particles under hydrotreating conditions, discharging a second vapor phase hydrocarbon stream, and discharging a second liquid phase hydrocarbon stream, wherein the first liquid phase hydrocarbon stream and the molecular hydrogen are contacted under a total pressure of less than 3,500 kilopascals-gauge, and wherein the molecular hydrogen is fed into the second vapor-liquid separator at a rate of no greater than 270 cubic meters of molecular hydrogen per cubic meter of the hydrocarbon feed, wherein the volume of molecular hydrogen and hydrocarbon feed are based on a temperature of 25° C. and a pressure of 101 kilopascals-absolute; (iii) a pyrolysis reactor adapted for receiving the first vapor phase hydrocarbon stream and the second vapor phase hydrocarbon stream, heating the first vapor phase hydrocarbon stream and the second vapor phase hydrocarbon stream to effect pyrolysis of at least a portion of the first vapor phase hydrocarbon stream and the second vapor phase hydrocarbon stream, and discharging a pyrolysis effluent stream; (iv) a quenching section adapted for receiving the pyrolysis effluent stream, quenching the pyrolysis effluent stream, and discharging a quenched pyrolysis effluent stream; (v) a third vapor-liquid separator adapted for receiving the quenched pyrolysis effluent stream, separating the quenched pyrolysis effluent stream to obtain a third vapor phase hydrocarbon stream comprising olefins and a third liquid phase hydrocarbon stream comprising pyrolysis tar, discharging the third vapor phase hydrocarbon stream, and discharging the third liquid phase hydrocarbon stream; and (vi) a hydroprocessing unit adapted for receiving the second liquid phase hydrocarbon stream and the third liquid phase hydrocarbon stream, hydroprocessing the second liquid phase hydrocarbon stream and the third liquid phase hydrocarbon stream under hydroprocessing conditions to produce a hydrocarbon fuel oil stream comprising less than 5,000 wppm of sulfur, and discharging the hydrocarbon fuel oil stream.

D2. The system of D1, wherein the second vapor-liquid separator comprises a flashing drum.

D3. The system of D1, wherein the second vapor-liquid separator comprises a flashing drum free of any internal structures.

D4. The system of D1, wherein the second vapor-liquid separator comprises a flashing drum, and wherein the flashing drum comprises internal structures disposed therein.

D5. The system of D4, wherein the internal structures comprise one or more trays, one or more packing materials, or a combination thereof.

D6. The system of any of D1 to D5, wherein second vapor-liquid separator is adapted to contact the hydrocarbon feed and the molecular hydrogen under a total pressure in a range of from 650 kilopascals-gauge to 1,750 kilopascals-gauge.

D7. The system of any of D1 to D6, wherein second first vapor-liquid separator is adapted to receive the molecular hydrogen at a rate of 36 m³ to 180 m³ of molecular hydrogen per cubic meter of the hydrocarbon feed.

D8. The system of any of D1 to D7, wherein second vapor-liquid separator is adapted to contact the hydrocarbon feed and the molecular hydrogen at a temperature of from 250° C. to 500° C.

D9. The system of any of D1 to D8, wherein second vapor-liquid separator is adapted to contact the hydrocarbon feed and the molecular hydrogen at a temperature of from 400° C. to 500° C.

D10. The system of any of D1 to D9, wherein second vapor-liquid separator is adapted to contact the hydrocarbon feed and the molecular hydrogen for a residence time of from 20 minutes to 2 hours.

D11. The system of any of D1 to D10, wherein the transition metal element is selected from vanadium, iron, cobalt, nickel, molybdenum, tungsten, and mixtures and combinations thereof.

D12. The system of any of D1 to D11, wherein the catalyst particles comprise a sulfide of the transition metal element.

D13. The system of any of D1 to D12, wherein the second vapor-liquid separator is adapted to receive the transition metal element in the catalyst particles at a feeding rate in a range of from 50 wppm to 500 wppm, based on the weight of the hydrocarbon feed.

D14. The system of any of D1 to D13, wherein the second vapor-liquid separator is adapted to receive the transition metal element in the catalyst particles at a feeding rate in a range of from 75 wppm to 250 wppm, based on the weight of the hydrocarbon feed.

D15. The system of any of D1 to D14, wherein the second vapor-liquid separator is adapted to receive the hydrocarbon feed and the catalyst particles at location(s) above the location at which the molecular hydrogen is adapted to be received.

D16. The system of any of D1 to D15, wherein the hydrocarbon feed comprises a resid.

D17. The system of any of D1 to D16, wherein the hydrocarbon feed comprises one or more plastic materials.

D18. The system of D17, wherein the hydrocarbon feed comprises from 1 wt % to 40 wt % of the one or more plastic materials based on the total weight of the hydrocarbon feed.

D19. The system of any of D1 to D18, wherein ≤10% of any aromatic rings present in the first liquid phase hydrocarbon stream are saturated in the second separate zone.

D20. The system of any of D1 to D19, wherein ≤50% of any sulfur present in the first liquid phase hydrocarbon stream is converted into $H_2S$ in the second separation zone.

D21. The system of any of D1 to D20, wherein ≤20% of any nitrogen in the first liquid phase hydrocarbon stream is converted into $NH_3$ in the second separation zone.

D22. The system of any of D1 to D21, further comprising a catalyst production vessel adapted for receiving a catalyst precursor and a sulfur source compound, forming the catalyst particles therein, and discharging the catalyst particles therefrom, wherein the catalyst particles comprise a sulfide of the transition metal element.

D23. The system of any of D1 to D22, further comprising a solid-liquid separator adapted for separating at least a portion of the catalyst particles from the first liquid phase hydrocarbon stream, discharging a catalyst-lean liquid phase, and discharging a catalyst-rich product.

D24. The system of any of D1 to D23, further comprising a fourth vapor-liquid separator adapted for receiving the hydrocarbon fuel oil stream, discharging a hydrotreated quench oil, and discharging a mid-cut solvent.

D25. The system of any of D1 to D24, wherein the quenching section comprises a transfer line exchanger, an indirect heat exchanger, or a combination thereof.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of this disclosure, other and further embodiments of this disclosure may be devised without departing from the basic scope thereof, and the scope thereof is determined by the claims that follow.

What is claimed is:

1. A process for converting a hydrocarbon feed by pyrolysis, comprising:
    (I) feeding the hydrocarbon feed, a plurality of catalyst particles, and molecular hydrogen into a separation zone, wherein the catalyst particles comprise a transition metal element;
    (II) contacting at least a portion of the hydrocarbon feed and at least a portion of the molecular hydrogen in the presence of the catalyst particles under hydrotreating conditions in the separation zone, wherein the hydrocarbon feed and the molecular hydrogen are contacted under a total pressure of less than 3,500 kilopascals-gauge, wherein the molecular hydrogen is fed into the separation zone at a rate of no greater than 270 cubic meters of molecular hydrogen per cubic meter of the hydrocarbon feed, and wherein the volume of molecular hydrogen and hydrocarbon feed are based on a temperature of 25° C. and a pressure of 101 kPa-absolute;
    (III) obtaining from the separation zone a vapor phase hydrocarbon stream and a liquid phase hydrocarbon stream; and
    (IV) feeding at least a portion of the vapor phase hydrocarbon stream into a pyrolysis reaction zone to produce a pyrolysis effluent comprising olefins and molecular hydrogen.

2. The process of claim 1, wherein the hydrocarbon feed and the molecular hydrogen are contacted in step (II) under a total pressure in the separation zone in a range of from 650 kilopascals-gauge to 1,750 kilopascals-gauge.

3. The process of claim 1, wherein the molecular hydrogen is fed into the separation zone at a rate of 36 m³ to 180 m³ of molecular hydrogen per cubic meter of the hydrocarbon feed.

4. The process of claim 1, wherein the hydrocarbon feed and the molecular hydrogen are contacted in step (II) at a temperature in the separation zone of from 250° C. to 500° C.

5. The process of claim 1, wherein the hydrocarbon feed and the molecular hydrogen are contacted in step (II) at a temperature in the separation zone of from 400° C. to 500° C.

6. The process of claim 1, wherein the hydrocarbon feed and the molecular hydrogen are contacted in step (II) for a residence time of from 20 minutes to 2 hours.

7. The process of claim 1, wherein the transition metal element is selected from vanadium, iron, cobalt, nickel, molybdenum, tungsten, and mixtures and combinations thereof.

8. The process of claim 1, wherein the catalyst particles comprise a sulfide of the transition metal element.

9. The process of claim 1, wherein the transition metal element in the catalyst particles is fed into the separation zone at a feeding rate in a range of from 50 wppm to 500 wppm, based on the weight of the hydrocarbon feed.

10. The process of claim 1, wherein the transition metal element in the catalyst particles is fed into the separation zone at a feeding rate in a range of from 75 wppm to 250 wppm, based on the weight of the hydrocarbon feed.

11. The process of claim 1, wherein the hydrocarbon feed and the catalyst particles are fed into the separation zone at location(s) above the location at which the molecular hydrogen is fed into the separation zone.

12. The process of claim 1, wherein the hydrocarbon feed comprises a resid.

13. The process of claim 1, wherein the hydrocarbon feed comprises one or more plastic materials.

14. The process of claim 1, wherein the hydrocarbon feed comprises crude oil or a fraction thereof and one or more plastic materials.

15. The process of claim 14, wherein the hydrocarbon feed comprises from 1 wt % to 40 wt % of the one or more plastic materials based on the total weight of the hydrocarbon feed.

16. The process of claim 1, wherein ≤10% of any aromatic rings present in the hydrocarbon feed are saturated in the separation zone.

17. The process of claim 1, wherein ≤50% of any sulfur present in the hydrocarbon feed is converted into $H_2S$ in the separation zone.

18. The process of claim 1, wherein ≤20% of any nitrogen present in the hydrocarbon feed is converted into $NH_3$ in the separation zone.

19. The process of claim 1, wherein the separation zone is a flashing drum, or a portion thereof.

20. The process of claim 1, further comprising:
    feeding a catalyst precursor and a sulfur source compound into a catalyst production vessel; and
    forming the catalyst particles comprising a sulfide of the transition metal element in the catalyst production vessel.

21. The process of claim 1, further comprising:
    obtaining from the pyrolysis effluent a pyrolysis tar stream; and
    feeding the pyrolysis tar stream and at least a portion of the liquid phase hydrocarbon stream into a hydroprocessing zone to produce a hydrocarbon fuel oil stream comprising less than 5,000 wppm of sulfur.

22. The process of claim 21, further comprising removing solid particles from the liquid phase hydrocarbon stream before feeding the at least a portion of the liquid phase hydrocarbon stream into the hydroprocessing zone.

23. The process of claim 21, further comprising:
    obtaining from the hydrocarbon fuel oil stream a mid-distillate stream; and recycling at least a portion of the mid-distillate stream to the hydroprocessing zone as a solvent.

24. A process for converting a hydrocarbon feed by pyrolysis, comprising:
(I) heating a hydrocarbon feed to produce a heated hydrocarbon feed comprising a vapor phase and a liquid phase;
(II) feeding the heated hydrocarbon feed into a first separation zone;
(III) obtaining from the first separation zone a first vapor phase hydrocarbon stream and a first liquid phase hydrocarbon stream;
(IV) feeding the first liquid phase hydrocarbon stream, a plurality of catalyst particles, and molecular hydrogen into a second separation zone, wherein the catalyst particles comprise a transition metal element;
(V) contacting at least a portion of the first liquid phase hydrocarbon stream and at least a portion of the molecular hydrogen in the presence of the catalyst particles under hydrotreating conditions in the second separation zone, wherein the first liquid phase hydrocarbon and the molecular hydrogen are contacted under a total pressure of less than 3,500 kilopascals-gauge, wherein the molecular hydrogen is fed into the second separation zone at a rate of no greater than 270 cubic meters of molecular hydrogen per cubic meter of the hydrocarbon feed, and wherein the volume of molecular hydrogen and hydrocarbon feed are based on a temperature of 25° C. and a pressure of 101 kilopascals-absolute;
(VII) obtaining a second vapor phase hydrocarbon stream and a second liquid phase hydrocarbon stream from the second separation zone; and
(VIII) feeding at least a portion of the first vapor phase hydrocarbon stream and at least a portion of the second vapor phase hydrocarbon stream into a pyrolysis reaction zone to produce a pyrolysis effluent comprising olefins and molecular hydrogen.

* * * * *